US008217110B2

(12) United States Patent
Melancon et al.

(10) Patent No.: US 8,217,110 B2
(45) Date of Patent: Jul. 10, 2012

(54) COLOR CHANGE CYANOACRYLATE ADHESIVES

(75) Inventors: Kurt C. Melancon, White Bear Lake, MN (US); George Van Dyke Tiers, Saint Paul, MN (US); Larry A. Lien, Woodbury, MN (US); Scott D. Pearson, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1190 days.

(21) Appl. No.: 11/850,873

(22) Filed: Sep. 6, 2007

(65) Prior Publication Data
US 2008/0075862 A1 Mar. 27, 2008

Related U.S. Application Data

(60) Provisional application No. 60/824,970, filed on Sep. 8, 2006.

(51) Int. Cl.
*C08L 39/00* (2006.01)
(52) U.S. Cl. ........ 524/555; 524/556; 524/773; 524/776; 526/297; 526/298
(58) Field of Classification Search .................. 524/555, 524/556, 773, 776; 526/297, 298
See application file for complete search history.

(56) References Cited

U.S. PATENT DOCUMENTS

| | | | |
|---|---|---|---|
| 3,646,135 A | 2/1972 | Coles et al. | |
| 3,742,018 A | 6/1973 | O'Sullivan | |
| 3,776,950 A | 12/1973 | Mitsch | |
| 3,856,552 A | 12/1974 | Deyak | |
| 3,874,884 A | 4/1975 | McKellar et al. | |
| 4,006,018 A | 2/1977 | Wiese, Jr. | |
| 4,149,852 A | 4/1979 | Tiru et al. | |
| 4,405,750 A * | 9/1983 | Nakata et al. ................. | 524/717 |
| 4,407,960 A | 10/1983 | Tratnyek | |
| 4,495,509 A | 1/1985 | Chao | |
| 4,751,020 A * | 6/1988 | Marten et al. ............ | 252/301.21 |
| 5,554,664 A | 9/1996 | Lamanna et al. | |
| 5,874,616 A | 2/1999 | Howells et al. | |
| 5,877,230 A | 3/1999 | Kutal | |
| 6,518,356 B1 | 2/2003 | Friese et al. | |
| 6,544,714 B1 * | 4/2003 | Bourdelais et al. ........... | 430/263 |
| 6,689,826 B2 | 2/2004 | Wojciak | |
| 6,835,789 B1 | 12/2004 | Kneafsey et al. | |
| 2003/0121448 A1* | 7/2003 | Chen et al. ................. | 106/31.18 |
| 2004/0034116 A1 | 2/2004 | Wojciak | |
| 2004/0254272 A1 | 12/2004 | Ando et al. | |
| 2005/0112085 A1 | 5/2005 | MacDonald et al. | |
| 2008/0145316 A1* | 6/2008 | MacDonald et al. ........ | 424/10.3 |

FOREIGN PATENT DOCUMENTS

| | | |
|---|---|---|
| EP | 1580200 A | 9/2005 |
| JP | 10-176142 | 6/1998 |
| WO | WO 02/30363 A2 | 4/2002 |

OTHER PUBLICATIONS

Gessner et al., "Triarylmethane and Diarylmethane Dyes", Ullmann's Encyclopedia of Industrial Chemistry [Online], Jun. 15, 2000, XP007903988, Retrieved from the Internet: URL: http://mrw.interscience.wiley.com/emrw_9783527306732/ueic/article/a27_179/current/html< [retrieved on Feb. 4, 2008] p. 9.
K. Hunger, "Industrial Dyes—Chemistry, Properties, Applications", 2003, Wiley, XP002467701, pp. 63-64, paragraph 2.6.3.
Barker et al., "Electronic Absorption Spectra of o-Methyl Derivatives of Michler's Hydrol Blue and Crystal Violet; Conformational Isomers of Crystal Violet" Steric Effect in Di- and Tri-arylmethanes. Part I pp. 3957-3963.
Hammett et al., "A Series of Simple Basic Indicators. I. The Acidity Functions of Mixtures of Sulfuric and Perchloric Acids with Water", Acidity Functions of Sulfuric and Perchloric Acids, Jul. 1932, pp. 2721-2739.
Hammett et al., "A Series of Simple Basic Indicators. II. Some Applications to Solutions in Formic Acid", Indicators in Formic Acid Solutions, Nov. 1932, pp. 4239-4247.
Hammett et al., "Some Properties of Electrolytes in the Solvent Sulfuric Acid" Contribution from the Department of Chemistry, Columbia University, vol. 55, May 6, 1933, pp. 1900-1909, New York City, NY.
Smith et al., "The Acidity of Buffered and Unbuffered Sulfuric Acid Solutions in Nitromethane", Contribution from the Department of Chemistry, Columbia University, vol. 67, Jan. 1945, Pittsburgh, PA pp. 23-30.
Arnett et al., "Solvent Effects in Organic Chemistry. II. Sulfolane[1]—A Weakly Basic Aprotic Solvent of High Dielectric Constant[2]", Contribution No. 1175 from the Department of Chemistry of the University of Pittsburgh, vol. 86, Feb. 5, 1964, Pittsburgh, PA, pp. 409-412.
Burwell et al., "Solvent Characteristics of Tetramethylene Sulfone" Communications to the Editor, Department of Chemistry, Northwestern University vol. 81, Jul. 20, 1959, Evanston, IL, pp. 3799-3800.
Preston-Thomas, H, "The International Temperature Scale of 1990 (ITS-90)", Metrologia, vol. 27, Springer-Verlag, 1990, pp. 3-10.
Birch et al., "Non-catalytic Reduction of Thiophens. Part I. Thiophen", Anglo-Iranian Oil Co. Ltd., Research Station, 1951, pp. 2556-2563.
Whitehead et al., "The Preparation and Physical Properties of Sulfur Compounds Related to Petroleum. II Cyclic Sulfides[2]", Contribution from the Research Department, Anglo-Iranian Oil Co. Ltd. vol. 73, Aug. 1951, pp. 3632-3635.
Paul et al., "$H_o$ and Related Indicator Acidity Functions", 1956, pp. 1-45.
Jorgenson et al., "A Critical Re-evaluation of the Hammett Acidity Function at Moderate and High Acid Concentrations of Sulfuric Acid. New $H_o$ Values Based Solely on a Set of Primary Aniline Indicators" Contribution from the Department of Chemistry, University of California, Berkeley 4, CA., Apr. 1963, pp. 878-883.

(Continued)

*Primary Examiner* — Fred M Teskin
*Assistant Examiner* — Marie Reddick
(74) *Attorney, Agent, or Firm* — Lisa P. Fulton

(57) ABSTRACT

A cyanoacrylate-based adhesive composition is disclosed. The cyanoacrylate-based adhesive composition includes a cyanoacrylate monomer, and a bleachable dye including a Michler's hydrol cation or derivatized Michler's hydrol cation, paired with a non-nucleophilic anion that provides a stable color to the cyanoacrylate-based adhesive.

8 Claims, No Drawings

OTHER PUBLICATIONS

Arnett et al., "Solvent Effects in Organic Chemistry. IV. The Failure of Tertiary Aromatic Amines as Hammett Bases", Contribution No. 1223 From the Department of Chemistry, University of Pittsburgh, Pittsburgh 13, PA., vol. 86, Jul. 5, 1964, pp. 2671-2677.

Marziano et al., "The $M_c$ Activity Coefficient Function of Acid-Base Equilibria. Part I. New Methods for Estimating $pK_a$, Values for Weak Bases", J.C.S. Perkin II, 1973, pp. 1915-1922.

Färcasiu et al. "Determination of acidity functions and acid strengths by $^{13}C$ NMR", Journal of Progress in Nuclear Magnetic Spectroscopy, vol. 29, 1996, pp. 129-168.

Bodlander et al., "Chemical Central Gazette Complete Repertoire for All Branches of Pure and Applied Chemistry", German Chemical Society, vol. 69, 1898, p. 1105.

Gessner, "Triarylmethane and Diarylmethane Dyes", Ullmann's Encyclopedia of Industrial Chemistry, (2012), pp. 425-478, vol. 37, Wiley-VCH Verlag GmbH & Co. KGaA, Weinheim.

Barker, "Electronic Absorption Spectra of o-Methyl Derivatives of Michler's Hydrol Blue and Crystal Violet; Conformational Isomers of Crystal Violet", Steric Effects in Di- and Tri-arylmethanes, Part I, (1959), pp. 3957-3963.

\* cited by examiner

COLOR CHANGE CYANOACRYLATE ADHESIVES

CROSS-REFERENCE TO RELATED APPLICATION

This application claims the benefit of U.S. Provisional Patent Application Ser. No. 60/824,970, filed on Sep. 8, 2006, which is incorporated by reference herein.

BACKGROUND

The present disclosure relates generally to color change cyanoacrylate adhesives and methods of using the same.

Cyanoacrylate adhesives, also known as "super glues," are a versatile family of adhesives known to cure in seconds and provide strong adhesion to a wide variety of surfaces. In spite of these noteworthy attributes, several issues exist that limit the popularity of this adhesive class with consumers.

One issue with cyanoacrylate adhesives is that these adhesives bond instantly with skin. This issue is compounded by the fact that cyanoacrylate adhesives are usually colorless and difficult to observe when applied to a substrate. The inability of the end-user to observe where the adhesive is (or is not), as well as whether the adhesive is cured, often leads to unintended bonding of skin to itself or other substrates.

Some cyanoacrylate adhesives are lightly tinted to provide the end-user some ability to discriminate where the adhesive has and has not been applied. However, these color tints are often so light that a thinly applied adhesive layer is not perceptible. Increasing the intensity of color tint so that the thinly applied adhesive layer is perceptible, results in the cured adhesive remaining visible on the completed project which may be objectionable to the consumer.

SUMMARY

In an exemplary implementation, cyanoacrylate-based adhesive compositions are disclosed that include a cyanoacrylate monomer and a bleachable dye such as, for example, a Michler's hydrol cation or Michler's hydrol cation derivative, that provides a stable color to the uncured cyanoacrylate-based adhesive when paired with a non-nucleophilic anion.

In another exemplary implementation, the method includes combining an appropriately stabilized cyanoacrylate monomer with a bleachable dye such as, for example, a Michler's hydrol cation or derivatized Michler's hydrol cation paired with a non-nucleophilic anion to form a dye pair. The stabilized cyanoacrylate monomer and dye pair forms a cyanoacrylate-based adhesive composition. The dye pair provides a stable color to the cyanoacrylate-based adhesive composition.

These and other aspects of the adhesives according to the subject invention will become readily apparent to those of ordinary skill in the art from the following detailed description together with the Examples.

DETAILED DESCRIPTION

Accordingly, the present disclosure is directed to color change cyanoacrylate adhesives and methods of using the same. In particular, the cyanoacrylate adhesive is colored in the uncured state and becomes colorless or light-colored upon cure. In another embodiment, the cyanoacrylate adhesive is a first color in the uncured state and changes to a second color upon cure. These color change adhesives can allow the end-user to easily observe the lay of the adhesive as it is dispensed, and additionally, affords a means of visually assessing uniformity of bond lines, as well as determining where excess adhesive has been applied. These color change adhesives can allow the end-user a means of indicating the state-of-the-cure of the adhesive. In one example, if during the gluing operation the adhesive is colored, it is not cured, and accordingly, when said adhesive is fully cured, it is colorless or lightly colored. Normally if exposed adhesive is colorless or lightly colored it is sufficiently cured so that it may be touched without fear of bonding to the skin. While the present invention is not so limited, an appreciation of various aspects of the invention will be gained through a discussion of the examples provided below.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the following specification and attached claims are approximations that all variation depending upon the desirable properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The term "polymer" will be understood to include polymers, copolymers (e.g., polymers formed using two or more different monomers), oligomers and combinations thereof, as well as polymers, oligomers, or copolymers that can be formed in a miscible blend.

The term "alkyl" refers to a straight or branched chain monovalent hydrocarbon radical optionally containing one or more heteroatomic substitutions independently selected from S, O, Si, or N. Alkyl groups generally include those with one to twenty atoms or from one to ten atoms. Alkyl groups may be unsubstituted or substituted with those substituents that do not interfere with the specified function of the composition. Substituents include alkoxy, hydroxy, mercapto, amino, alkyl substituted amino, or halo, for example. Examples of "alkyl" as used herein include, but are not limited to, methyl, ethyl, n-propyl, n-butyl, n-pentyl, isobutyl, and isopropyl, and the like.

The phrase "stable color" will be understood to mean that a color or color intensity that visually persists for at least 14 days as measured by the test method described in the Examples herein. For example, a flowable cyanoacrylate adhesive is said to possess a "stable color" if the color or color intensity (e.g., blue color) visually persists for at least 14 days in a sealed container. In some embodiments, the samples remain usefully colored for a period of at least six months, or at least 1 year, or at least 2 years.

Unlike conventional pH indicators which are sequentially reversible, i.e., reversing color upon sequential exposure alternately to acid and to base, the bleachable dyes of the present invention tend to bleach irreversibly when formulated in color change cyanoacrylate compositions.

The cyanoacrylate-based adhesive composition described herein includes a cyanoacrylate monomer and a bleachable dye cation paired with a non-nucleophilic anion that provides the bleachable dye with a stable color. As this cyanoacrylate-based adhesive cures, it becomes colorless or lightly colored. In many embodiments, the bleachable dye cation paired with a non-nucleophilic anion is blended with the cyanoacrylate monomer prior to being applied to a substrate. In some embodiments, the bleachable dye cation paired with a non-nucleophilic anion is not blended with the cyanoacrylate monomer before the cyanoacrylate monomer is disposed on a substrate. In these embodiments, the bleachable dye cation paired with a non-nucleophilic anion can be disposed on the substrate and then the cyanoacrylate monomer is disposed on the bleachable dye cation paired with a non-nucleophilic anion.

The bleachable dye cation or cations can be chosen to produce any color, as desired. In many embodiments, the bleachable dye cation produces a blue or deep blue color. In many embodiments, the bleachable dye cation is formed from a Michler's hydrol (i.e., 4,4'-bis(dimethylamino)benzhydrol) or a derivative thereof.

Michler's hydrol or 4,4'-bis(dimethylamino)benzhydrol) is commercially available (from Sigma-Aldrich, St. Louis, Mo. 63103) and has the following chemical structure:

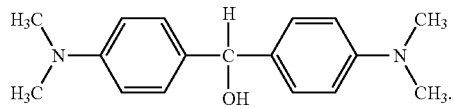

Michler's hydrol is a dye base and is colorless in its free (pure) form, and because this dye base by virtue of its amine substituents is nucleophilic, and as such will cause immediate polymerization of cyanoacrylate monomer, it is acidified prior to introduction into the cyanoacrylate described herein. When acidified, Michler's hydrol cation provides a blue (cyan) color: the color intensity varying with the acidified dye concentration. Selection of the appropriate acid stabilizer or non-nucleophilic anion to maintain dye (color) stability upon aging is described below. While not being bound by any particular theory, it is believed that Michler's hydrol cation is a dye that is degraded (e.g., bleached) concomitant with curing of the cyanoacrylate adhesive composition.

Derivatized Michler's hydrol can be used for the bleachable dye cation. Useful derivatized Michler's hydrols include, for example, the following molecules:

bis[4-(4-morpholinyl)phenyl]methanol (CAS#123344-13-8) having a chemical structure:

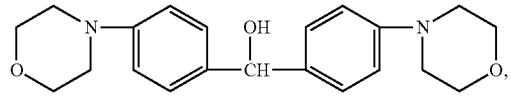

1,1-bis(4-dimethylaminophenyl)ethanol (CAS#33905-89-4) having a chemical structure:

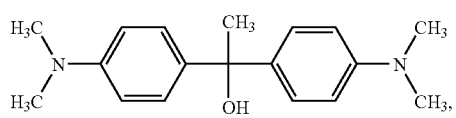

1,1-bis(4-dimethylaminophenyl)ethylene (CAS# 22057-85-8) having a chemical structure:

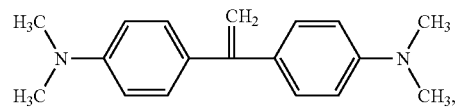

(It is believed that this compound is converted by proton addition to the methylene group into the same bleachable dye cation as provided by the preceding structure.)

bis(4-dimethylamino)-2-methylphenyl)methanol) (CAS#43001-46-3) having a chemical structure:

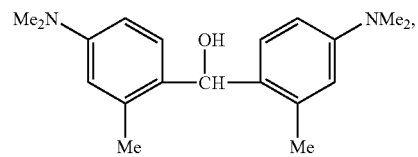

bis(3-bromo-4-dimethylaminophenyl)methanol having a chemical structure:

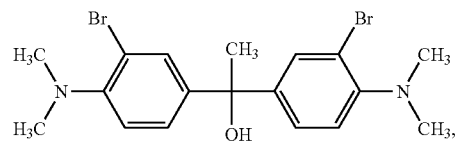

N-[bis(4-dimethylaminophenyl)methyl]morpholine (CAS#21295-86-3) having a chemical structure:

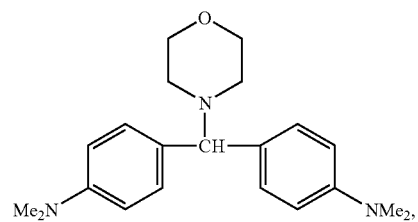

N-[bis[4-(dimethylamino)phenyl]methyl]-N'-n-butyl-urea (CAS#27086-41-5) having a chemical structure:

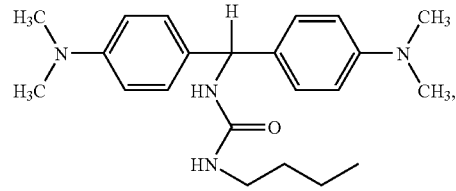

N-[bis[4-(dimethylamino)phenyl]methyl]-N'-(4-ethoxyphenyl)-urea (CAS#37171-10-1) having a chemical structure:

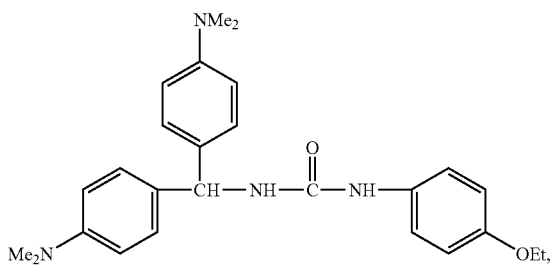

N-[bis[4-(dimethylamino)phenyl]methyl]-N'-(4-methylphenyl)-urea (CAS#123344-13-8) having a chemical structure:

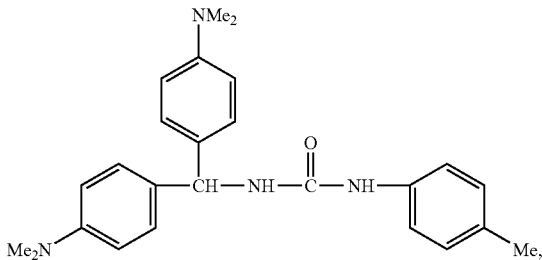

N-[bis[4-(dimethylamino)phenyl]methyl]-N'-phenyl-urea (CAS#34851-49-5) having a chemical structure:

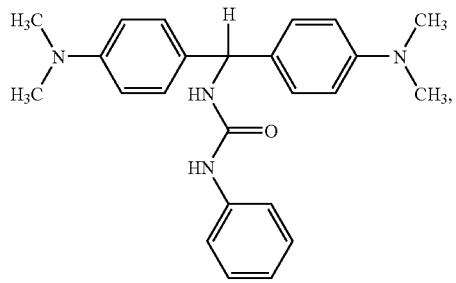

N-[bis[4-(dimethylamino)phenyl]methyl]-aniline (CAS# 6245-51-8) having a chemical structure:

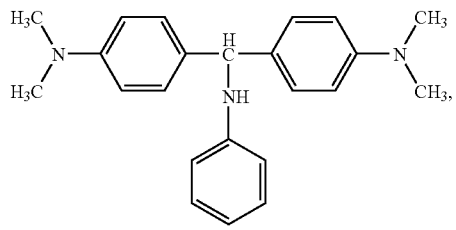

N-[bis[4-(dimethylamino)phenyl]-methyl]-benzenesulfonamide (CAS# 3147-38-4) having a chemical structure:

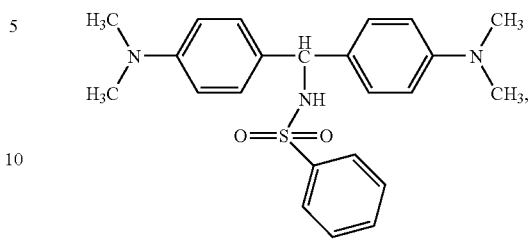

These Michler's hydrol derivatives are either commercially available or described in U.S. Pat. Nos. or Publication Nos. 4,407,960; 3,874,884; 3,856,552; 4,006,018; 3,646,135; and 2005-1488010, all of which are incorporated by reference herein.

The bleachable dye cation can be present in the cyanoacrylate adhesive in any useful amount. In many embodiments, the bleachable dye cation can be present in the cyanoacrylate adhesive in an amount from 1 ppm or greater, or 10 ppm or greater, or 50 ppm or greater, or 100 ppm or greater, or 250 ppm or greater, or 500 ppm or greater, or 1000 ppm or greater. In some embodiments, the bleachable dye cation can be present in the cyanoacrylate adhesive in an amount from 1 ppm to 1000 ppm, or from 10 to 500 ppm, or from 1 to 100 ppm.

The non-nucleophilic anion is typically derived from acids of high strength. The strength of such acids is often classified by means of Acidity Indicators, i.e., members of a series of increasingly weak nitrated aniline bases that provide a readily measured color change upon protonation. The accepted measure of the "strength" of aqueous acidic solutions is pH, the negative logarithm of the hydrogen ion concentration (or activity), and $pK_A$, which similarly is the negative logarithm of the ionization constant $K_A$, in aqueous solution, of weak to moderately strong acids. For extremely strong acids these means of description fail, as strong acids react with water, acting as a base, to form hydronium ion, $H_3O^+$, thus preventing the expression of higher acidities. For the measurement of the ultimate proton-donating acidity of pure anhydrous acids, the $H_o$ (Hammett Acidity Function) scale was created (L. P. Hammett & A. J. Deyrup, J. Amer. Chem. Soc., 54 2721, 4239 (1932), 55 1900 (1933)). Its numerical scale was provided by stepwise dilution of each acid by water until the composition fell within the measurable pH range, thus it was termed an extension of the pH scale. Color-indicating very weak bases were provided, for which the protonated forms had non-aqueous pH-like behavior that could be inter-related by stepwise overlap. While useful, the $H_o$ scale provides no common non-aqueous medium for comparisons, as each anhydrous acid differs in solvent properties. Nearly all common "good" solvents are protonated by, or are reactive toward, very strong acids. Furthermore, to retain both neutral and ionic species in solution, a relatively high dielectric constant is accepted as necessary. Nitromethane appeared to be such a solvent (L. C. Smith & L. P. Hammett, J. Amer. Chem. Soc., 67 23 (1945)), but failed to provide simple buffer equilibria; this behavior was (and remains) unexplained.

The Hammett Acidity Function is applied to pure or nearly pure acids, a situation extremely different from the use in solution in a cyanoacrylate monomer. It is appropriate therefore to evaluate acid strengths in a polar organic solvent by a means analogous to ordinary aqueous buffer systems, which depend on the strength of the acids employed.

Anhydrous "Sulfolane" (tetramethylene sulfone; tetrahydrothiophene-1,1-dioxide; CAS RN 126-33-0), is an acid-inert non-dissociating good solvent of high dielectric constant, 44, (E. M. Arnett & C. F. Douty, J. Amer. Chem. Soc., 86 409 (1964)), and has the further advantage that the melting point is a sensitive measure of its water content (R. L. Burwell Jr & C. H. Langford, J. Amer. Chem. Soc., 81 3799 (1959)). Although requiring rigorous purification to remove traces of water, and impurities that are severely discolored by strong acids, it does appear to yield simple buffer and color-indicator equilibria.

Therefore we create the non-aqueous analog of the common buffer system by combining equimolar amounts of a very strong acid and its salt in anhydrous sulfolane, and evaluate the buffered acid's strength by means of an Acidity Indicator, I. (For such an aqueous 1:1 buffer the aqueous pH is equal to the $pK_A$ for the aqueous acid.) The procedure to conduct such measurements is described in detail in the Test Methods section of this disclosure. Strength of an acid buffer of any composition may for simplicity be expressed by means of the ratio of molar extinction coefficients, $\in$, and $\in^*$, where $\in$ is the molar extinction coefficient of an Acidity Indicator, I, in the acid-free solvent, sulfolane, and $\in^*$ is the apparent molar extinction coefficient of that Acidity Indicator in a buffered test solution (as described in the Test Methods section) according to the following equations:

$$\text{Extinction Ratio} = \in^*/\in = N \text{ and } (\in-\in^*)/\in = C = (1-N)$$

For an Equimolar (1:1) Buffer, for which the Strength Ratio, $E=(\in-\in^*)/\in$ (for a specified Acidity Indicator, I), E expresses the strength of the acid itself. To exhibit this relative to the strength of the conjugate acid, $IH^+$, of the Acidity Indicator it is convenient to use the familiar negative logarithmic form: $pA=-\log(E/N)=+\log(N/E)$.

Given a "$pK_I$" for the (conjugate acid) strength of an Acidity Indicator, the strength of a buffer's acid on that scale becomes "$pK_A$", where "$pK_A$"="$pK_I$"+pA. Such a single self-consistent scale is provided computationally for all of the Acidity Indicators as described under Indicators in the Test Methods section.

For a workable carbon-acid the Strength Ratio, E, defined as $(\in-\in^*)/\in$, for a chosen 1:1 buffer system in the sulfolane solvent described above, is greater than 0.1 (corresponding to "$pK_A$"<+2.0), preferably greater than 0.25 (corresponding to "$pK_A$"<+1.5) when the indicator I is 4-methoxy-2-nitroaniline. For a workable non-carbon-acid, for example an oxyacid, the acid Strength Ratio E, as measured in the sulfolane solvent described above, is greater than 0.2, preferably greater than 0.5 (corresponding to "$pK_A$"<-1.0), when the indicator is 4-chloro-2-nitroaniline, or more preferably greater than 0.50 (corresponding to "$pK_A$"<-2.3) when the indicator is 2-chloro-6-nitroaniline, or even more preferably greater than 0.5 (corresponding to "$pK_A$"<-5.4) when the indicator is 2,6-dinitroaniline. The mathematically equivalent Acid Strength measure, "$pK_A$", applicable to all buffer ratios, is described in the Test Methods section. It enables the Strength Ratio, E, to be ascertained by means of titration.

Carbon-acids differ qualitatively in being extremely much weaker than acids bearing the acidic hydrogen on, for example, oxygen or nitrogen, as is well established in the scientific literature. It is unusual for a carbon-acid to possess sufficient acid strength to be measurable using the nitrated aniline Acidity Indicators utilized herein. For a carbon-acid to be this strong it is necessary that its anion be non-nucleophilic. As compared to the strong non-carbon-acids which homopolymerize epoxy compounds, the observation that these relatively weaker carbon-acids also homopolymerize epoxy compounds demonstrates the comparably non-nucleophilic nature of their anions.

The non-nucleophilic anion can include an $\alpha,\beta$-highly fluorinated or perfluorinated($C_1$-$C_8$)alkylsulfonate anion. In further embodiments, the non-nucleophilic anions include those derived from bis($\alpha,\beta$-highly fluorinated or perfluorinated-sulfonyl)methane, tris($\alpha,\beta$-highly fluorinated or perfluorinated-alkylsulfonyl)methane, bis($\alpha,\beta$-highly fluorinated or perfluorinated-alkylsulfonyl)imide, or mixtures thereof. In yet further embodiments, the non-nucleophilic anion may be formed from trifluoromethanesulfonic acid, nonafluorobutanesulfonic acid, fluorosulfonic acid, bis(trifluoromethanesulfonyl)methane (methylene disulfone), bis(trifluoromethanesulfonyl)imide(imide acid), bis(pentafluoroethanesulfonyl)imide (ethylimide acid), tris(trifluoromethanesulfonyl)methane (methide acid), boron trifluoride bis-acetic acid, and other boron trifluoride complexes such as the etherate, methanol, propanol, and tetrahydrofuran derivatives. Similar reagents that react, decompose, or hydrolyze to form any of the above recited acids are also useful. Combinations of the acids from which the aforementioned non-nucleophilic anions are derived may also be useful in the practice of this invention. In some embodiments, the non-nucleophilic anion is formed from trifluoromethanesulfonic acid, methide acid, boron trifluoride methanol, boron trifluoride bis-acetic acid, imide acid, and/or ethylimide acid. In certain preferred embodiments, the non-nucleophilic anion is formed from imide acid, boron trifluoride bis-acetic acid, and/or methide acid.

The non-nucleophilic anion can be present in the cyanoacrylate adhesive in any useful amount. In many embodiments, the acid of the non-nucleophilic anion can be present in the cyanoacrylate adhesive in an acid/dye mol ratio from 1 to 5, or from 1 to 2.5. In certain embodiments, the acid of the non-nucleophilic anion can be present in the cyanoacrylate adhesive in an acid/dye mol ratio from 1 to 5, or from 1 to 3, or from 1.5 to 2.5. With careful formulation, the presence of lesser amounts (equivalents) of certain nucleophilic anions may sometimes be tolerated.

Cyanoacrylate adhesives described herein include, for example, 2-cyanoacrylates such as, for example, methyl-2-cyanoacrylate, ethyl-2-cyanoacrylate, propyl-2-cyanoacrylate, isopropyl-2-cyanoacrylate, butyl-2-cyanoacrylate, isobutyl-2-cyanoacrylate, amyl-2-cyanoacrylate, hexyl-2-cyanoacrylate, cyclohexyl-2-cyanoacrylate, octyl-2-cyanoacrylate, 2-ethylhexyl-2-cyanoacrylate, allyl-2-cyanoacrylate, propargyl-2-cyanoacrylate, phenyl-2-cyanoacrylate, benzyl-2-cyanoacrylate, methoxyethyl-2-cyanoacrylate, ethoxyethyl-2-cyanoacrylate, tetrahydrofulfuryl-2-cyanoacrylate, 2-chloroethyl-2-cyanoacrylate, 3-chloropropyl-2-cyanoacrylate, 2-chlorobutyl-2-cyanoacrylate, 2,2,2-trifluoroethyl-2-cyanoacrylate, hexafluoroisopropyl-2-cyanoacrylate, and/or the like. In many embodiments, these reactants are substantially/effectively anhydrous.

The cyanoacrylate-based adhesive compositions described herein are liquid or gels (if a sufficient amount of thickener is combined) prior to curing. In many embodiments, the liquid or flowable cyanoacrylate-based adhesive compositions have a viscosity in a range from 1 to 5000 cP, as desired.

The color change 2-cyanoacrylate-based adhesive composition described herein can optionally include an additional colorant, a radical polymerization stabilizer, a thickener, a curing accelerator, a crosslinker, a plasticizer and/or a thixotropic agent, as desired. Desirably all additives should be substantially anhydrous and free of nucleophilic compounds that may be deleterious to the bleachable color stability, the viscosity stability or both. Furthermore, the selection of the acidic compounds influence curing speed and product life of 2-cyanoacrylate-based compositions. Thus, selection of their suitable amounts to be added and combination can be determined by taking into account target curing performance, product life, color change performance and various other aspects.

The additional colorant can be provided to achieve change in colors from a first colored state to a second colored state as the color change cyanoacrylate-based adhesive progresses from an uncured state to a cured state. The additional colorant can be any useful dye or pigment. In some embodiments the additional colorant is an indicator dye (not a bleachable dye such as Michler's hydrol or derivative) that can further change color as the cyanoacrylate-based adhesive progresses from an uncured state to a cured state. In some embodiments, the additional colorant includes two or more pigments or dyes, depending on a desired color (in the cured or uncured state). The change in color of the cyanoacrylate-based adhesive from a first colored uncured state to a final colored cured state, or from a first colored uncured state to a final colorless cured state can be used to indicate the progress of the curing reaction or change in the cyanoacrylate-based adhesive. Visual color standards may be prepared and provided as a reference to the reaction progress. For example, a simple series of three printed color-matched dots that diminish in intensity as the concentration of acidified Michler's hydrol cation in the curing adhesive diminishes might be useful in determining whether the adhesive was curing properly, and furthermore aid in identifying whether the initial composition was sufficiently unpolymerized to be a useful adhesive composition.

The radical polymerization stabilizer can include hydroquinone, hydroquinone monomethyl ether, catechol, pyrogallol and the like. In some embodiments, the radical polymerization stabilizer can be present in the range of 1 ppm by weight to 1% by weight.

In order to decrease bonding time, anion polymerization accelerators can be added to uncured cyanoacrylate adhesives, which include polyalkylene oxides and their derivatives, crown ethers and their derivatives, silacrown ethers and their derivatives, calixarene derivatives, thiacalixarene derivatives and the like, and combinations or blends of any of the aforementioned classes of accelerators. Some useful accelerants are disclosed in U.S. Pat. No. 6,835,789 and incorporated herein to the extent it does not conflict. In some embodiments, the accelerant is present in the range from 200 to 5000 ppm. Nucleophilic polymerization accelerators, e.g., amines such as N,N-dimethyl-p-toluidine solutions may also be applied to adherend surfaces prior to application of an uncured cyanoacrylate adhesive in order to accelerate cure of the adhesive.

Thermal performance of cyanoacrylate adhesives is typically improved by the addition of crosslinkers, i.e., multifunctional monomers which upon or subsequent to cure crosslink the polymerizing adhesive. Useful crosslinkers may include biscyanoacrylates, allyl-2-cyanoacrylate, propargyl-2-cyanoacrylate, multi-functional acrylates and (meth)acrylates, and combinations of the aforementioned.

The thickener can include viscosity modifiers, gel formers, thixotropic, and/or polymeric additives such as, for example, polymethylmethacrylate (PMMA), methyl methacrylate/acrylate copolymers, methyl methacrylate/methacrylate copolymers, cellulose derivatives, fumed silica, hydrophobic silica, and the like. In some embodiments, the thickener can be added in the range of 0.1 to 20% by weight. In some embodiments, the thickener can be added to provide a viscosity in a range from 5 to 5000 cP. In certain embodiments, the thickener can be added to provide a viscosity in a range from 2500 to 100,000 cP. In some embodiments, PMMA and fumed silica are combined in the composition to form a cyanoacrylate adhesive gel.

The plasticizer can be added to adjust modulus of the adhesive from a rigid adhesive to a toughened or flexible adhesive. Plasticizers can include, for example, phthalate esters, citrate esters, glycerol triacetate, specific multifunctional (meth)acrylates and the like. In some embodiments, the plasticizer can be added in the range of 0.01 to 30% by weight.

In addition, perfumes, fillers, crosslinking agents, polymerization initiators, organic solvents or the like can optionally be added, as desired.

The present invention should not be considered limited to the particular examples described herein, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

TEST METHODS

Set Time

Set time was determined by depositing a single drop of cyanoacrylate adhesive (hereinafter "CA") on a glass microscope slide, overlapping a second slide atop the first, and applying modest finger pressure on the top slide in the bonding region to create a thin glue line. At the time the bond line is closed (2nd slide put in place) a stop watch is started. While holding the 1st slide, the 2nd slide non-bonded end is moved slowly from side to side over a small range of motion, of no more than 30 degrees, to determine when it can no longer be moved. When slide 2 can no longer be moved, the time on the stopwatch is recorded as the set time.

Color Assessment

A quantitative color assessment was performed to determine if changes occurred in sample color over time. This quantitative assessment was conducted by comparing the example to known colorimetric standards consisting of aqueous methylene blue solutions (preferably acidified by acetic acid) at concentrations of $2.0 \times 10^{-4}$ M, $1.5 \times 10^{-4}$ M, $1.0 \times 10^{-4}$ M, and $0.5 \times 10^{-4}$ M, packaged in the same quantity and bottle type as the experimental samples. A quantitative color scale of 0, 1, 2, 2.5 and 3 was employed where 3 corresponds to the deepest blue and 0 corresponds to colorless. Methylene blue concentrations of 2-, 1.5-, 1.0-, and $0.5 \times 10^{-4}$ M correspond to color ratings of 3, 2.5, 2, and 1 respectively. A colorless sample would be rated 0.

Bleaching

Bleaching was assessed at the conclusion of the set time test described above. In this case samples were visually inspected approximately 1 hour after conducting the set time test and identified as either "colorless", if they bleached colorless, or "tinted", if color or hue remained. Results from this test are labeled "Set Time Bleach".

Acid Strength Determination

The objective of this test method is to establish the strength of the acid being tested, as expressed, for example, in a half-neutralized "buffer" solution in purified sulfolane (tetramethylene sulfone), from which the strength is revealed by UV-Vis spectrometry to determine degree of protonation of an Acidity Indicator, I, and expressed relative to it as the Strength Ratio, E. More generally the mathematically equivalent Acid Strength, "$pK_A$", available from buffers of all ratios, or by titration, may be used to calculate the Strength Ratio.

Purification of Sulfolane

For this test method, sulfolane having a mp of at least 26.0° C., or preferably at least 28.0° C., or more preferably greater than or equal to 28.4° C. relative to the mp of 99.999% pure gallium, 29.765° C., (measured using a thermometer so calibrated) and being substantially transparent, i.e., giving a stable near-zero absorbance baseline when this sulfolane is present in the sample cell, with pure water in the reference cell of a double beam spectrophotometer over the region 350-550 nm, is required. For this and all subsequent absorbance measurements the reading at 550 nm should be found to be near zero.

For this test method, not even the best commercial "Reagent" or "99+%" sulfolane is suitable. Less pure grades (if wet, they can be first improved by storing with KOH pellets) can be brought to "Reagent" level by crystallizing below 20° C., then allowing to slowly melt at 25° C.-27° C. with frequent or continuous drainage of the melt liquid, which can be recycled. The portion remaining solid and/or the commercial "99+%" sulfolane, is subjected to the following purification regimen. To avoid freezing of the purified sulfolane during handling, it is advisable to maintain the work area at or above 30° C.

To a stoppered 500 ml Erlenmeyer flask, fitted with a Bunsen valve or other pressure-relief device, is placed 300 to 350 g of the "99+%" sulfolane and 1.58 g $KMnO_4$. The liquid, initially deep magenta, develops a brown cast (from $MnO_2$). It is warmed on a hot plate held at 45-55° C. for at least 5 days, with additional 1 g portions of $KMnO_4$ being added as needed to maintain a weak magenta color. The liquid is decanted away from any settled solids and centrifuged (filtration is difficult) to remove $MnO_2$. The supernatant liquid is decanted into a 500 ml Erlenmeyer flask with pressure-relief stopper, and to it is added 15 g of a previously-prepared drying mixture, which had been made at least one day earlier by shaking together in a well sealed bottle equal weights of phosphorus pentoxide and 100-200 mesh silica gel that had been dried at 170° C. overnight. The flask of sulfolane and drying mixture is heated for at least 1 week on a hot plate at 100° C. and soon turns to an amber-brown color. It is then cooled and the very dark liquid decanted into a 250 ml distilling flask. To control "bumping" during distillation it is desirable to add 10 to 15 fluoropolymer PFA (or FEP) tubes, of outside diameter about 3 mm, inside diameter about 1 mm, sealed off at their tops, and of a length greater than the flask diameter.

The flask, heated by a heating mantle, is surmounted by a simple vacuum fractional distillation unit, comprising first a short Vigreux column section (to intercept "bumped" liquid) and above it a section containing a 20 cm length of ¼" Pyrex helices, or preferably a 10 cm long section containing POD-BIELNIAK HELIPAK, ⅛", stainless steel, either contents being available from Wilmad-LabGlass, Elk Grove Village, Ill. Above it is a standard vacuum distillation head with reflux style condenser and thermometer, and stopcocks positioned to allow controlled take-off, plus exchange and re-evacuation of receptor flasks, specifically without breaking the vacuum of the distillation column. Only minimal insulation of the column or head by means of a few paper towels wrapped around the hot parts is needed, with provision for observation of a tendency to "flood" in the packed section, as it may be alleviated by blowing air on the distilling flask. The entire distilling apparatus should be assembled with 24/40 standard taper joints fitted with PTFE conical sleeves and made vacuum tight throughout with perfluorinated vacuum grease, available as KRYTOX LVP, from E. I. du Pont de Nemours and Company, Wilmington, Del., in order to resist hot sulfolane vapor.

For vacuum distillation an ordinary oil pump capable, with liquid nitrogen trap, of exhausting the system to 0.05 Torr., is needed, to enable sulfolane to distill at 68-75° C., as much higher pressure and temperature may produce discoloration. The system pressure is continuously monitored by means of an electronic vacuum gauge reading with reasonable precision from 0.010 Torr. to 1.0 Torr. Water flow through the condenser must be restricted, as the distillate will freeze and plug it below 30° C., with hazardous consequences.

Distillation should become relatively stable around 73° C./0.10 Torr., and a large center cut of 130-150 g should be taken at 72° C./0.090 Torr. to 68° C./0.050 Torr. This cut, upon crystallization in its ca. 150 mL receiver flask, should upon warming show melting of its last crystals at 2° C., or preferably 1.5° C., or more preferably 1° C. below the melting point of 99.999% gallium metal, 29.765° C., one of several pure-metal melting points that officially define the Celsius temperature scale, as explained by H. Preston-Thomas et al., Metrologia 27 3 (1990). The literature melting point, 28.86° C., given without reference to one another by S. F. Birch and D. T. MacAllan, J. Chem. Soc. (London) 2556 (1951) and by E. V. Whitehead, R. A. Dean and F. A. Fidler, J. Amer. Chem. Soc. 73 3632 (1951), and allegedly obtained by extrapolation from lower temperature data, is indefensible in view of direct gallium-based measurement of 29.0° C. minimum.

Sulfolane has a low heat of fusion, as given by R. L Burwell Jr. and C. H. Langford, J. Amer. Chem. Soc., 81 3799 (1959), and therefore has an extremely large freezing point depression, thus providing an upper limit on water content, increasing by 0.031 m in water content for each 1.00° C. reduction in melting point.

Nevertheless, sulfolane does not have to be treated with excessive care, as it is virtually nonvolatile at atmospheric pressure, thus cannot condense moisture by evaporative cooling, nor lose weight by evaporation, when handled briefly in open vials. Little or no water is absorbed from the air, as shown by slow change at the 0.01 mg level of weight of an open vial of sulfolane on the balance. The measurable, although not large, effect on spectroscopic acidity measurements produced by addition of 1 microliter of water (ca. 1.00 mg), to a test sample of approximately 2.5 g, permits ready estimation of the negligible effect of brief unprotected exposure of samples to air at 30° C. and 20 to 40% relative humidity.

Acidity Indicators

For the purpose of this work, visibly colored neutral Acidity Indicator molecules which lose color reversibly upon accepting a proton from a strong acid are used. To minimize inconsistency of electronic effects, the selection is restricted to various substituted 2-nitroanilines, for which a second nitro group, if present, must be in the 6-position. It is a characteristic shared by all members of this group thus far examined that the neutral form has a clean symmetrical absorbance peak in the range 380-460 nm, which disappears (reversibly) for its protonated form. Thus, the fractional loss in intensity represents the reduction in concentration of the neutral Acidity Indicator, (I), the reduction representing ($IH^+$). This is readily measured by a spectrophotometer, or even by a properly filtered colorimeter.

In principle all Acidity Indicators might have their indicator constants in sulfolane related by the stepwise overlap method as has been done, and variously revised, for measuring $H_o$ as reported in the cited references.

M. A. Paul & F. A. Long, Chem. Rev. 57 1 (1957)

M. J. Jorgenson & D. R. Hartter, J. Amer. Chem. Soc., 85 878 (1963)

E. M. Arnett & G. W. Mach, J. Amer. Chem. Soc., 86 2671 (1964)

N. C. Marziano, G. C. Cimino, & R. C. Passerini, J. Chem. Soc. (London) Perkin II, 1915 (1973)

D. Farcasiu & A. Ghenciu, J. Prog. Nucl. Mag. Spect. 29 129 (1996)

In practice that approach is narrow in scope and suffers from cumulative procedural and experimental variability. An alternative system, used here, which is entirely objective, self-consistent and reproducible, relies experimentally on the effects of acidity on chosen specified Acidity Indicators. For convenience, these may be related numerically by means of their computed "$pK_A$" values, which may be generated for all known and predicted 2-nitroaniline derivatives by employing a computational method provided by Advanced Chemistry Development, Inc (ACD/Labs), Toronto, ON, Canada, www.acdlabs.com. This software is ACD/$pK_a$ Batch, version 9-04, ACD/Labs© 1994-2007. (Identical "$pK_A$" values were generated by their Versions 8-14 and 8-19). The "$pK_A$" values may be accessed through the Chemical Abstracts Service. These Acidity Indicator "$pK_A$" values are here termed "$pK_I$" for clarity.

Experimental spectrophotometric data are used to calculate logarithmic acidity values ("pH", analogous to pH) that are helpful in determining E by titration. To avoid confusion with aqueous pH and pK values, and with the many literature $H_o$ values which they resemble, the logarithmic acidity values in anhydrous sulfolane are designated "pH", and the derived acid strength constants "$pK_A$". One may identify the indicator(s) on which the "$pK_A$" are based, by virtue of being close to their computational "$pK_I$" values.

The indicators chosen for the present work, together with their computational "$pK_I$" values are shown in Table A.

TABLE A

Chosen Acidity Indicators and Their Computed "$pK_I$" Values

| Chemical Name | CAS Ref. No. | "$pK_I$" |
|---|---|---|
| 4-Methoxy-2-nitroaniline | 96-96-8 | 0.96 |
| 4-Methyl-2-nitroaniline | 89-62-3 | 0.46 |
| 2-Nitroaniline* | 88-74-4 | −0.23 |
| 4-Chloro-2-nitroaniline* | 89-63-4 | −1.00 |
| 5-Bromo-2-nitroaniline | 5228-61-5 | −1.53 |
| 2-Chloro-6-nitroaniline* | 769-11-9 | −2.34 |
| 2,4-Dichloro-6-nitroaniline* | 2683-43-4 | −3.08 |
| 4-(Methylsulfonyl)-2-nitroaniline | 21731-56-6 | −3.88 |
| 2-Chloro-6-nitro-4-(trifluoromethyl)aniline | 57729-79-0 | −4.62 |
| 2-Bromo-6-nitro-4-(trifluoromethyl)aniline | 113170-71-1 | −4.74 |
| 2,6-Dinitroaniline* | 606-22-4 | −5.45 |
| 4-Chloro-2,6-dinitroaniline* | 5388-62-5 | −6.03 |
| 2,6-Dinitro-4-(trifluoromethyl)aniline | 445-66-9 | −7.42 |
| 2,6-Dinitro-4-(methylsulfonyl)aniline | 42760-39-4 | −8.88 |

To minimize the effects of spectrophotometric uncertainty at the extremes, it is strongly recommended that the absorbance measurements fall between 15% and 75% of the value expected if the indicator were completely non-protonated, i.e., in its neutral form. For the six indicators identified with an asterisk in Table X, the computed "$pK_I$" values differ only by about 0.1 $pK_A$ unit from the experimentally measured (and revised) $pK_A$ values reported in the literature references cited above, thus supporting the validity of the computational method. Additional computed "$pK_I$" values for indicators presumed to be useful are listed in Table B.

TABLE B

Additional Acidity Indicators Presumed Useful and Their "$pK_I$" Values

| Chemical Name | CAS Ref. No. | "$pK_I$" |
|---|---|---|
| 2,4-Dimethoxy-6-nitroaniline | 57715-92-1 | 0.87 |
| 2,4-Dimethyl-6-nitroaniline | 1635-84-3 | 0.27 |
| 4-(Methylthio)-2-nitroaniline | 23153-09-5 | −0.09 |
| 2-Methoxy-6-nitroaniline | 16554-45-3 | −0.35 |
| 2-Methyl-6-nitroaniline | 570-24-1 | −0.44 |
| 3-(Methylthio)-2-nitroaniline | 351458-30-5 | −0.86 |
| 4-Bromo-2-nitroaniline | 875-51-4 | −1.05 |
| 4-Chloro-2-methoxy-6-nitroaniline | 859877-49-9 | −1.09 |
| 2-Chloro-4-methoxy-6-nitroaniline | 29105-95-1 | −1.12 |
| 4-Bromo-2-methoxy-6-nitroaniline | 77333-45-0 | −1.14 |
| 2-Bromo-4-methoxy-6-nitroaniline | 10172-35-7 | −1.24 |
| 2-(Methylthio)-6-nitroaniline | 494226-39-0 | −1.36 |
| 2-Nitro-4-(trifluoromethoxy)aniline | 2267-23-4 | −1.38 |
| 5-Chloro-2-nitroaniline | 1635-61-6 | −1.46 |
| 2-Nitro-4(trifluoromethylthio)aniline | 404-74-0 | −2.34 |
| 2-Bromo-6-nitroaniline | 59255-95-7 | −2.46 |
| 2-Nitro-4-(trifluoromethyl)aniline | 400-98-6 | −2.54 |
| 2-Nitro-6-(trifluoromethoxy)aniline | 235101-48-1 | −2.55 |
| 2,4-Dibromo-6-nitroaniline | 827-23-6 | −3.25 |
| 2-Nitro-6-(trifluoromethyl)aniline | 24821-17-8 | −3.37 |
| 2,6-Dinitro-4-methoxyaniline | 5350-56-1 | −4.66 |
| 2,6-Dinitro-4-methylaniline | 6393-42-6 | −4.93 |
| 2-Nitro-4-(trifluoromethylsulfonyl)aniline | 400-23-7 | −5.30 |
| 4-Bromo-2,6-dinitroaniline | 62554-90-9 | −6.21 |
| 4-Cyano-2,6-dinitroaniline | 61313-43-7 | −8.48 |
| 2,4,6-Trinitroaniline | 489-98-5 | −9.30 |
| 2,6-Dinitro-4-(trifluoromethylsulfonyl)aniline | 19822-30-1 | −10.40 |

Calculations of "pH" and "$pK_A$" Values

The straightforward method of L. C. Smith and L. P. Hammett, J. Amer. Chem. Soc. 67 23 (1945), is used to calculate "pH" and "$pK_A$" for the systems of interest. For each Acidity Indicator chosen the Molar Extinction Coefficient, $\in$, is calculated from the absorbance of its sulfolane solution, preferably made up exactly as for the acidity measurement, but omitting the acid. The equation then takes the form:

$$\in = AMG/SUD = AYG/U$$

where:
A=Absorbance measured
M=Molecular weight of the indicator
G=Weight in grams of sample solution
S=Weight fraction of solid indicator in its sulfolane concentrate
U=Weight in mg of indicator concentrate used
D=Density of the sample solution, normally 1.2622
Y=Batch constant for an indicator concentrate (=M/SD)

The needed density of the reference solution is most easily established by use of a small Ostwald-Sprengel pycnometer of approximately 0.5 to 2 ml volume which has been calibrated against water. To fill the pycnometer by suction its tip may be dipped into the test solution in the cell after the spectral measurement has been made.

For a sample including an acid (or its buffer) its apparent extinction coefficient, $\in^*$, is related to its observed absorbance, $A^*$, by the same equation. The fraction of neutral indicator (I) remaining is $N=\in^*/\in$, and the corresponding fraction of its conjugate acid ($IH^+$) is $C=(1-N)=(\in-\in^*)/\in$.

The acidity "pH" is given by: "pH"="$pK_I$"+log(N/C) where "$pK_I$" is the computed "$pK_A$" for the indicator, generated by ACD/Labs software Version 9-04, as cited above.

For a titration or buffer solution, comprising B millimoles of base and F millimoles of non-neutralized "free" acid, F=T−B, T being the total millimoles of acid used (if B is added as the salt of T, thus not neutralizing T, F=T). From this, the "$pK_A$" for the acid is: "$pK_A$"="pH"+log(F/B)

This, together with the preceding equations, constitutes the mathematical interconvertibility of the Acid Strength, "$pK_A$", and the Strength Ratio, E. The Strength Ratio, E, is based upon experimentally known ratios, F/B, resulting from accurate weighings and the presumption that the morality of T is correct. If the acid of T is significantly impure, corrections must be made. For an inert impurity the value of T is simply reduced to T', and F'=T'−B. If, however, as is often the case, the impurity is the salt of the acid (typically the hydronium salt, $H_3O^+$ $A^-$) then this must also be part of the total base, B'=B+(T−T') and the ratio becomes:

Ratio=$F'/B'=F'/(B+T-T')=(T'-B)/(B+T-T')$

For a given very strong acid sample, originally "pure" (free from metallic salts, etc) the existing impurity is normally water. The effective purity, T'/T, may be estimated by (gravimetric) titration in anhydrous sulfolane with an anhydrous weighable base. Note that unknown but limited amounts of water present in the sulfolane will partially "neutralize" a very strong acid and modify the titration and "$pK_A$" calculation accordingly, but will not change the validity of the resulting "$pK_A$".

In order to find the half-neutralized "1:1 Buffer" mid-point, at which E is defined, one needs to ascertain the end-point with reasonable confidence. This requires an indicator having a "$pK_A$" two or three units less acidic than "pH" measured for a (supposedly) equimolal buffer, such that the titrated "pH" is within (passes through) the "best" indicator range, namely N=∈*/∈ between 0.15 and 0.75. Such an end-point is reliable.

Imidazole, readily soluble in sulfolane, is normally an excellent choice as the titration or buffer-making base. Results agree with those from ethyldiisopropylamine, despite the latter's volatility and its very limited solubility in sulfolane. They also agree with those from the additive bases, $CF_3SO_3^-Na^+$ and $CF_3SO_3^-$ $(Bu_4N)^+$, these of course being limited to $CF_3SO_3H$. In view of its low molecular weight, a 1.000 molal concentrate of imidazole in sulfolane is recommended.

Acidity measurements are best made with F and B about 0.1 m or lower, for solubility reasons and to keep the sulfolane, as the solvent medium, in great excess. At greater dilution of very strong acids, extremely dry sulfolane is needed to minimize interference.

A list of "$pK_A$" values thus measured for acids of interest in stabilization of bleachably-colored cyanoacrylate adhesives is in Table C.

TABLE C

| Acid Strength, "$pK_A$" | | |
|---|---|---|
| Chemical Structure | "$pK_A$" | 95% Confidence Limits |
| $(CF_3SO_2)_2NH$ | −6.6 | ±0.2 |
| $(C_2F_5SO_2)_2NH$ | −6.6 | ±0.5 |
| $CF_3SO_3H$ | −6.1 | ±0.5 |
| $BF_3 \cdot 2CH_3CO_2H$ | −3.0 | ±0.1 |
| $BF_3 \cdot 2CH_3OH$ | −0.5 | ±0.02 |
| $BF_3 \cdot 2H_2O$ | −0.2 | ±0.1 |
| $CH_3SO_3H$ | 1.26 | ±0.06 |
| $CF_3CO_2H$ | 3.15 | ±0.06 |
| $(CF_3SO_2)_3C^- (H_2O)_{16}H^+$ | 0.93 | ±0.30 |
| $(CF_3SO_2)_2C(H)C_6H_5$ | 0.97 | ±0.04 |
| $(CF_3SO_2)_2CH_2$ | 1.32 | ±0.06 |

Use of Titration to Determine Acid Strength, "$pK_A$", of a Strong Acid, and Consequent Strength Ratios. The Strength Ratio, E, defined as (∈−∈*)/∈ for a chosen 1:1 buffer system, $HA:A^-$, plus indicator $IH^+:I$, in sulfolane solvent, is not correct unless the true concentrations of HA and $A^-$ are known to be equal. This is best ascertained and verified by gravimetric-spectrophotometric titration, to determine the true concentration of the strong acid component in the measurement sample, as described below.

A stock solution is made from 0.28133 g of pure, colorless sublimed crystals of methylene disulfone, MDS, and sulfolane to total 9.99476 g. In a stoppered 1 cm fused silica spectrophotometric cell is placed 2.41146 g. of the stock solution. It contains 67.877 mg (T=0.24228 mmol) of MDS, plus 23.29 mg indicator concentrate, U, to total G grams. The indicator concentrate is made by dissolving 6.07 mg of 4-Methoxy-2-nitroaniline (molecular wt. M=168.15, "$pK_I$"=+0.96) in sulfolane to total 2193.78 mg, giving S=0.002767 and thus Y=48147. (The value of this indicator was determined to be 5497 by spectrophotometry on a diluted solution in sulfolane.) The absorbance at the indicator's spectral maximum, 446 nm, is only 0.022, relative to the reference cell containing only the stock solution.

Titration is begun by adding a small drop, 14.46 mg, of 1.0000 m sulfolane solution of purified imidazole, which thus adds 0.01446 mmol of base, B, producing absorbance 0.158. Additional increments of the imidazole solution are added, with the results shown in Table D.

TABLE D

| Results of Titration to Determine E for MDS | | | | | | | |
|---|---|---|---|---|---|---|---|
| Increment # & imidazole (mg) | Total g in cell, G | Total mmol (=g) of B | Ratio B/T | Absorbance A | C = (ε − ε*)/ε | "pH" | "$pK_A$" (MDS) |
| 1 (14.46) | 2.44914 | 0.01446 | 0.0597 | 0.158 | 0.8545 | 0.19? | 1.39? |
| 2 (18.26) | 2.46740 | 0.03272 | 0.1351 | 0.284 | 0.7365 | 0.51 | 1.32 |
| 3 (20.72) | 2.48812 | 0.05344 | 0.2206 | 0.396 | 0.6295 | 0.73 | 1.28 |
| 4 (21.28) | 2.50940 | 0.07472 | 0.3084 | 0.495 | 0.5329 | 0.90 | 1.25 |
| 5 (30.21) | 2.53961 | 0.10493 | 0.4331 | 0.610 | 0.4174 | 1.10 | 1.22 |
| 6 (44.44) | 2.58405 | 0.14937 | 0.6165 | 0.757 | 0.2644 | 1.40 | 1.20 |
| 7 (50.31) | 2.63436 | 0.19968 | 0.8242 | 0.891 | 0.1173 | 1.84 | 1.17 |
| 8 (21.04) | 2.65540 | 0.22072 | 0.9110 | 0.948 | 0.0533 | 2.21? | 1.20? |
| 9 (25.62) | 2.68102 | 0.24634 | 1.0168 | 0.983 | 0.0089 | 3.01?? | (—) |

?indicates substantial uncertainty resulting from the extreme absorbances

The average of the six most reliable "$pK_A$" values is 1.24±0.05 (95% confidence limits). The sudden increase in "pH" signals the end-point of the titration, which is seen to occur at B/T=1.0 as expected for a pure acid. The mid-point (buffer ratio 1:1) most reliable value for the Strength Ratio, E=0.34, is calculated from "$pK_A$"=1.24, and "$pK_I$"=0.96 by the equation: E=1/[1+antilog("$pK_A$"−"$pK_I$")]. (By interpolation of C values, E may be approximated as 0.36.)

Materials

Unless otherwise noted, all materials were or can be obtained from Sigma-Aldrich Corp., St. Louis Mo.

"PR01" refers to 2-ethylcyanoacrylate, 100 cP, super fast cure, 10-30 second set time, available from Chemence, Inc., Alpharetta, Ga. 30005.

"SB20" refers to 2-ethylcyanoacrylate, 5 cP, ethyl hybrid, 0-20 sec set time, high strength bonds on acidic surfaces, available from Chemence, Inc., Alpharetta, Ga. 30005.

"SB14" refers to 2-ethylcyanoacrylate, 100 cP, 10-60 second set time, high strength bonds on plastic and rubber, available from Chemence, Inc., Alpharetta, Ga. 30005.

"RX-100" refers to 2-ethylcyanoacrylate, 100 cP, non-surface sensitive, 10-30 sec set time, available from Pacer Technology, Rancho Cucamonga, Calif. 91730.

"TX-100" refers to 2-ethylcyanoacrylate, 100 cP, 10-30 sec set time, available from Pacer Technology, Rancho Cucamonga, Calif. 91730.

"NO100" refers to 2-methoxy-ethoxy-α-cyanoacrylate, 100 cP, no odor, no frost, 30-50 sec set time, available from Pacer Technology, Rancho Cucamonga, Calif. 91730.

"HC150" refers to 2-isopropylcyanoacrylate, 150 cP, low chlorosis, high clarity, better moisture resistant than ethylcyanoacrylates, 10-30 sec set time, available from Pacer Technology, Rancho Cucamonga, Calif. 91730.

SCOTCH-WELD cyanoacrylate adhesives, available from 3M, Maplewood, Minn. 55144 are listed in Table E below:

TABLE E

Scotchweld Cyanoacrylate Adhesives

| Product | Chemistry | Viscosity (cP) | Set Time (sec) |
| --- | --- | --- | --- |
| SCOTCH-WELD CA-40 | 2-ethylcyanoacrylate | 2-10 | 1-30 |
| SCOTCH-WELD CA-4 | 2-ethylcyanoacrylate | 60-120 | 5-40 |
| SCOTCH-WELD CA-40H | 2-ethylcyanoacrylate | 400-600 | 5-40 |
| SCOTCH-WELD CA-5 | 2-ethylcyanoacrylate | 2000-3000 | 20-70 |
| SCOTCH-WELD CA-7 | 2-methylcyanoacrylate | 15-40 | 1-30 |
| SCOTCH-WELD CA-8 | 2-ethylcyanoacrylate | 70-120 | 5-40 |
| SCOTCH-WELD CA-9 | 2-ethylcyanoacrylate | 1000-1700 | 20-70 |
| SCOTCH-WELD CA-100 | 2-ethylcyanoacrylate | 2500-4500 | 20-70 |
| SCOTCH-WELD CA-50 | 2-ethylcyanoacrylate | gel | 60-120 |

SCOTCH Super Glue Liquid, catalog number AD110, 2-ethylcyanoacrylate, available from 3M, St Paul, Minn., 55144.

"NEXCARE props Liquid Bandage", n-butyl cyanoacrylate, 5 cP, 30-60 sec set time, available from 3M, St. Paul, Minn. 55144

Michler's hydrol, recrystallized from toluene, mp 102-102.5° C., available from Sigma-Aldrich, St. Louis, Mo. 63103.

Bis(trifluoromethanesulfonyl)methane "methylene disulfone" "MDS", synthesized using the procedures disclosed in U.S. Pat. No. 3,776,950.

Bis(trifluoromethanesulfonyl)imide "imide acid", synthesized using the procedures disclosed in U.S. Pat. No. 5,874,616.

Bis(pentafluoroethanesulfonyl)imide "ethylimide acid", synthesized using the procedures disclosed in U.S. Pat. No. 5,874,616.

Trifluoromethanesulfonylamide "sulfonyl amide", synthesized using the procedures disclosed in U.S. Pat. No. 5,874,616.

Tris(trifluoromethanesulfonyl)methane, "methide acid", 58.4% solids aqueous, synthesized using the procedures disclosed in U.S. Pat. No. 5,554,664.

Boron trifluoride-methanol complex in excess methanol, about 50 wt % $BF_3$, (corresponding to $BF_3$:2 $CH_3OH$) available from Sigma-Aldrich Corp., St. Louis Mo.

Boron trifluoride-acetic acid complex, 98%, available from Sigma-Aldrich Corp., St. Louis Mo.

Bis-(3-bromo-4-dimethylaminophenyl)methanol—The ketone, 4,4'-bis-(dimethylamino)-3,3'-dibromobenzophenone (E. Grimaux, Comptes Rendus de l'Academie des Sciences, 126 1117-1118, [1898]; Chemisches Centralblatt [5F., 2J.] 1898, I, p. 1105), is reduced using 3% sodium mercury amalgam in aq. ethanol by the method of C. C. Barker et al., J. Chem. Soc. (London), 3962-63 [1959], to give bis-(3-bromo-4-dimethylaminophenyl)methanol. This product gives an intense blue color upon dissolution in acetic acid, as shown by Barker et al., on p. 3963, thus verifying reduction of ketone to hydroxyl. The structure is further confirmed by NMR.

Dye base concentrate A—9 pt methyl acetate and 1 pt Michler's hydrol.

"MSA Concentrate"—solution consisting of 1.8 pt PR01 and 0.2 pt methanesulfonic acid.

"TFMSA Concentrate"—solution consisting of 1.8 pt PR01 and 0.2 pt triflic acid (i.e., trifluoromethanesulfonic acid).

Microscope slide, VWR Cat #48300-025, selected precleaned, 25×75×1 mm thick.

Lexan™ polycarbonate sheeting 2.9 mm thick, cut into 26.5 mm×103 mm coupons, available from GE Plastics, Pittsfield, Mass. 01201.

Pronto™ Surface Activator, acetone solution of N,N-dimethyl-p-toluidine, available from 3M, St. Paul, Minn. 55144.

EXAMPLES

Unless otherwise noted, all example formulations are provided in parts by weight.

Example 1 and Comparative Example 1

A variety of commercially available cyanoacrylate compositions were converted to colored-cure indicating compositions by adding a dye masterbatch to each. The dye masterbatch was prepared by first formulating a 10 wt % dye base solution of Michler's hydrol in ethyl acetate and a 10 wt % acid solution of triflic acid in PR01. The 10 wt % dye base solution contained 1.35 part ("pt") ethyl acetate and 0.15 pt Michler's hydrol. The acid solution contained 1.8 pt PR01 and 0.2 pt triflic acid. The dye masterbatch was prepared by combining 9.4 pt PR01, 0.366 pt 10% triflic acid solution, and mixing well, before adding 0.3 pt 10% dye base solution and mixing to complete the preparation and obtain a dye masterbatch having an acid/dye mol ratio of approximately 2.2/1 which contained approximately 3000 ppm dye. The final samples were made by combining, in a HDPE bottle, 0.25 pt of the dye masterbatch with 10 pt of the commercial cyanoacrylates shown in Table 1 to provide samples having a final dye content of approximately 75 ppm.

The resulting samples were all deep blue in color. Set time was assessed as described in the Test Methods section, and shows that set time is essentially unaltered in these compositions by the addition of the dye masterbatch. In the set time test all of the samples bleached from deep blue to colorless upon cure. These results show that acid/dye combinations of the present invention are suitable to convert a wide variety of commercially available cyanoacrylate adhesive into color change compositions.

TABLE 1

Set time of Color Change Cyanoacrylate Adhesives

| Example | Commercial CA | Sample No Dye | Set Time Dyed | Set Time Bleach |
|---|---|---|---|---|
| 1A | SCOTCH-WELD CA40 | 1 | 1-2 | colorless |
| 1B | SCOTCH-WELD CA4 | 7 | 4 | colorless |
| 1C | SCOTCH-WELD CA40H | 4 | 3-4 | colorless |
| 1D | SCOTCH-WELD CA5 | 18-20 | 17-20 | colorless |
| 1E | SCOTCH-WELD CA7 | 1 | 1 | colorless |
| 1F | SCOTCH-WELD CA8 | 2-3 | 3 | colorless |
| 1G | SCOTCH-WELD CA9 | 5-7 | 5 | colorless |
| 1H | SCOTCH-WELD CA100 | 35 | 35-40 | colorless |
| 1I | PR01 | 7 | 7 | colorless |
| 1J | RX-100 | 3-4 | 3-4 | colorless |
| 1K | TX-100 | 3-4 | 5 | colorless |
| 1L | NO-100 | 20 | 11-15 | colorless |
| 1M | HC-150 | 25-35 | 30-60 | colorless |

Comparative Example 1 demonstrates that upon cure, pentamethoxy red (PMR), one of the dyes of US 2004/0254272 A1, does not bleach to a colorless form when employed as shown in Example 1. A 2% solution of PMR in ethyl acetate was prepared and 0.25 pt of this PMR solution was added to 9.75 pt PR01 to provide solution PMR-CA containing approximately 500 ppm PMR dye in PR01. Upon standing for 15 minutes sample PMR-CA thickened considerably, in 30 minutes was completely gelled, and in 2 hr was solid. This result shows that such a solution can not be made without adding a complementary charge of acid to the system for stability purposes.

To circumvent gelation of the dye masterbatch, a PMR dye concentrate masterbatch was made by stabilizing PR01 with triflic acid prior to introducing the PMR dye. In this preparation a 10% PMR solution, PMR-10, was prepared by combining 1.35 pt methyl acetate and 0.15 pt PMR. PR01, TFMSA Concentrate, and PMR-10 were combined in a ratio 9.58 pt to 0.165 pt to 0.3 pt respectively to create a dye concentrate, PMR-3000, having an acid/dye molar ratio of approximately 1.5/1 and containing approximately 3000 ppm dye. This solution was made by first combining PR01 and TFMSA Concentrate in a HDPE container and mixing well to obtain a homogenous solution followed by addition of the PMR-10 solution and additional mixing to homogeneity. Dye masterbatch PMR-3000 was further diluted with PR01 to provide sample PMR-500, containing approximately 500 ppm PMR, by combining 8.34 pt PR01 and 1.66 pt PMR-3000 and mixing to homogeneity.

Final samples were prepared as in Example 1 by adding 0.5 pt PMR-500 solution to 4.5 g of the various SCOTCHWELD cyanoacrylates and PR01, shown in Table C1, to provide comparative examples having a dye content of approximately 50 ppm. All of the resulting comparative samples were purple in color, and were tested for initial set time and bleaching as described in the Test Methods section. The results are presented in Table C1, which show that although set times of all the samples are generally reasonable, perhaps some of the samples exhibit a slowing of cure, none of these PMR-containing comparative samples bleached colorless upon cure, i.e., all the examples retained a purple tint after cure. This is in contrast to the samples prepared in Example 1, based on Michler's hydrol, where upon cure all samples bleached completely in the set time test.

TABLE C1

Set time of Pentamethoxy Red Containing Cyanoacrylate Adhesives

| Example | Commercial CA | Initial Set Time (sec) | Set Time Bleach |
|---|---|---|---|
| C1A | SCOTCH-WELD CA40 | 2 | tinted |
| C1B | SCOTCH-WELD CA4 | 4 | tinted |
| C1C | SCOTCH-WELD CA40H | 4 | tinted |
| C1D | SCOTCH-WELD CA5 | 9 | tinted |
| C1E | SCOTCH-WELD CA7 | 2 | tinted |
| C1F | SCOTCH-WELD CA8 | 4 | tinted |
| C1G | SCOTCH-WELD CA9 | 20-30 | tinted |
| C1H | SCOTCH-WELD CA100 | >60 | tinted |
| C1I | PR01 | 7 | tinted |

Example 2 and Comparative Example 2

This example examines the solution and color stability of color change cyanoacrylate compositions based on a variety of different organic and fluorochemical acids. Dye masterbatches employing each acid were prepared by first formulating a 10% solution of each acid in PR01. The acid solutions contained the components and quantities shown in Table 2 (in parts by weight).

TABLE 2

Acid Concentrates

| Acid | PR01 | Acid |
|---|---|---|
| borontrifluoride etherate | 1.35 | 0.15 |
| trifluoromethanesulfonic acid | 1.35 | 0.15 |
| methylene disulfone | 1.35 | 0.15 |
| methide acid | 1.24 | 0.26 |
| imide acid | 1.35 | 0.15 |
| ethylimide acid | 1.35 | 0.15 |
| trifluoromethanesulfonic anhydride | 1.35 | 0.15 |
| trifluoroacetic acid | 1.35 | 0.15 |
| trichloroacetic acid | 1.35 | 0.15 |
| sulfuric acid (96%) | 1.35 | 0.15 |
| hydrochloric acid (36%) | 1.08 | 0.42 |
| phosphoric acid (85%) | 1.32 | 0.18 |
| nitric acid (69%) | 1.35 | 0.15 |
| sulfonyl amide | 1.35 | 0.15 |
| methanesulfonic acid (98%) | 1.35 | 0.15 |
| dodecylbenzenesulfonic acid | 1.35 | 0.15 |

The acid concentrates prepared in Table 2 were mixed with PR01 and dye base concentrate A in the proportions (in parts by weight) shown in Table 3 to prepare dye masterbatches. This was accomplished by adding the acid concentrate to PR01 in a HDPE bottle and mixing well for 15 minutes on a rotary agitator prior to introducing the dye concentrate. Following the addition of dye base concentrate the samples were placed back on the rotary agitator and allowed to mix at ambient temperature. All of the samples were charged to provide a dye concentration of approximately 3000 ppm and an acid/dye mol ratio of approximately ~2/1, with the exception of trifluoromethanesulfonic anhydride which had a 1/1 anhydride/dye mol ratio. Inspecting the samples after 30 minutes of mixing revealed that Comparative Examples C2A-Master through C2G-Master had all either solidified or gelled, and thus were discarded. With respect to C2A-Master and C2B-Master the anions of the acids alone are too nucleophilic, and therefore cause gelling. In the cases of Comparative Examples C2C-Master through C2F-Master, containing water, when compared to 2D-Master containing about 40% water, which did not cause gelling, it is apparent that the anions of the acids employed in Masters C2C-Master through C2F-Master were the causes of gelling, not the water content. Regarding C2G-Master, although slightly acidic, it fails to stabilize the dye, in contrast to its imide acid, 2E-Master. With respect to C2I-Master, it is considered to closely resemble C2H-Master with respect to nucleophilicity of its anion. It is expected that other fluorine-free organic sulfonic acids will be equivalent to these in anion nucleophilicity.

TABLE 3

Dye Masterbatches

| Example | Acid | PR01 | Acid Concentrate | Dye Base Concentrate A |
|---|---|---|---|---|
| 2A-Master | borontrifluoride etherate | 4.723 | 0.157 | 0.15 |
| 2B-Master | trifluoromethanesulfonic acid | 4.715 | 0.167 | 0.15 |
| 2C-Master | methylene disulfone | 4.585 | 0.311 | 0.15 |
| 2D-Master | methide acid | 4.453 | 0.457 | 0.15 |
| 2E-Master | imide acid | 4.584 | 0.312 | 0.15 |
| 2F-Master | ethylimide acid | 4.484 | 0.423 | 0.15 |
| 2G-Master | trifluoromethanesulfonic anhydride | 4.724 | 0.157 | 0.15 |
| C2A-Master | Trifluoroacetic acid | 4.751 | 0.127 | 0.15 |
| C2B-Master | Trichloroacetic acid | 4.702 | 0.181 | 0.15 |

TABLE 3-continued

Dye Masterbatches

| Example | Acid | PR01 | Acid Concentrate | Dye Base Concentrate A |
|---|---|---|---|---|
| C2C-Master | sulfuric acid (96%) | 4.767 | 0.109 | 0.15 |
| C2D-Master | hydrochloric acid (36%) | 4.829 | 0.040 | 0.15 |
| C2E-Master | phosphoric acid (85%) | 4.767 | 0.109 | 0.15 |
| C2F-Master | nitric acid (69%) | 4.802 | 0.070 | 0.15 |
| C2G-Master | sulfonyl amide | 4.716 | 0.165 | 0.15 |
| C2H-Master | methanesulfonic acid (98%) | 4.769 | 0.107 | 0.15 |
| C2I-Master | dodecylbenzenesulfonic acid | 4.539 | 0.362 | 0.15 |

The remaining dye masterbatches were all deep blue colored fluids and were further employed to formulate colored cure indicating cyanoacrylate compositions by mixing 0.25 pt dye masterbatch with 9.75 pt PR01, as described in Example 1 to provide samples having a final dye content of approximately 75 ppm. The resulting samples were divided into equal portions in separate HDPE bottles and one aged at ambient conditions and the other at 49° C. As the samples aged, qualitative viscosity observations were made to determine if viscosity was stable or increasing, by inverting the bottle and observing the adhesive flow. Color of the samples was also monitored during aging, as described in the Test Methods section of this document. The viscosity and color assessment results are shown in Tables 4 through 7. Set time data was monitored periodically and results obtained reported in Table 8.

TABLE 4

Viscosity of Color Change CAs Aged at 49° C.

| Example | Parent Acid | 3 day | 7 day | 14 day | 28 day | 56 day |
|---|---|---|---|---|---|---|
| 2A | boron trifluoride etherate | liquid | Liquid | liquid | no flow | gel |
| 2B | trifluoromethanesulfonic acid | liquid | Liquid | liquid | liquid | liquid |
| 2C | methylene disulfone | liquid | Liquid | liquid | liquid | liquid |
| 2D | methide acid | liquid | liquid | liquid | liquid | liquid |
| 2E | imide acid | liquid | liquid | liquid | liquid | liquid |
| 2F | ethylimide acid | liquid | liquid | liquid | liquid | liquid |
| 2G | trifluoromethanesulfonic anhydride | liquid | liquid | liquid | liquid | viscous |
| C2H | methanesulfonic acid | solid | solid | — | — | — |
| C2I | dodecylbenzenesulfonic acid | hi visc | solid | — | — | — |

TABLE 5

Viscosity of Color change CAs Aged at Room Temperature

| Example | Parent Acid | 3 day | 7 day | 14 day | 28 day | 56 day |
|---|---|---|---|---|---|---|
| 2A | boron trifluoride etherate | liquid | liquid | liquid | no flow | solid |
| 2B | trifluoromethanesulfonic acid | liquid | liquid | liquid | liquid | liquid |
| 2C | methylene disulfone | liquid | liquid | liquid | liquid | liquid |
| 2D | methide acid | liquid | liquid | liquid | liquid | liquid |
| 2E | imide acid | liquid | liquid | liquid | liquid | liquid |
| 2F | ethylimide acid | liquid | liquid | liquid | liquid | liquid |
| 2G | trifluoromethanesulfonic anhydride | liquid | liquid | liquid | liquid | gel |
| C2H | methanesulfonic acid | liquid | hi visc | no flow | — | — |
| C2I | dodecylbenzenesulfonic acid | liquid | slight visc increase | slow flow | — | — |

TABLE 6

Color Stability of Color Change CAs Aged at Room Temperature

| Example | Parent Acid | Initial | 7 day | 14 day | 28 day | 56 day |
|---|---|---|---|---|---|---|
| 2A | boron trifluoride etherate | 3.00 | 3.00 | 3.00 | 0 | 0 |
| 2B | trifluoromethanesulfonic acid | 3.00 | 3.00 | 3.00 | 3.00 | 1.50 |
| 2C | methylene disulfone | 3.00 | 3.00 | 3.00 | 3.00 | 2.50 |
| 2D | methide acid | 2.75 | 3.00 | 2.50 | 2.25 | 1.50 |
| 2E | imide acid | 3.00 | 3.00 | 3.00 | 3.00 | 2.50 |
| 2F | ethylimide acid | 3.00 | 3.00 | 3.00 | 3.00 | 2.50 |
| 2G | trifluoromethanesulfonic anhydride | 3.00 | 3.00 | 3.00 | 3.00 | 0.00 |
| C2H | methanesulfonic acid | 3.00 | 0.00 | 0.00 | — | — |
| C2I | dodecylbenzenesulfonic acid | 3.00 | 0.50 | 0.00 | — | — |

TABLE 7

Color Stability of Color change CAs Aged at 49° C.

| Example | Parent Acid | Initial | 7 day | 14 day | 28 day | 56 day |
|---|---|---|---|---|---|---|
| 2A | boron trifluoride etherate | 3.00 | 3.00 | 3.00 | 1 | 0 |
| 2B | trifluoromethanesulfonic acid | 3.00 | 3.00 | 3.00 | 3.00 | 2.00 |
| 2C | methylene disulfone | 3.00 | 3.00 | 3.00 | 3.00 | 2.50 |
| 2D | methide acid | 2.75 | 3.00 | 2.50 | 2.25 | 2.00 |
| 2E | imide acid | 3.00 | 3.00 | 3.00 | 3.00 | 2.50 |
| 2F | ethylimide acid | 3.00 | 3.00 | 3.00 | 3.00 | 2.50 |
| 2G | trifluoromethanesulfonic anhydride | 3.00 | 3.00 | 3.00 | 3.00 | 0 |
| C2H | methanesulfonic acid | 3.00 | 0.00 | — | — | — |
| C2I | dodecylbenzenesulfonic acid | 3.00 | 0.00 | — | — | — |

The results in Tables 4 through 7 show that Comparative Examples C2H and C2I provide only limited stability as both of these Examples cured in the bottle during heat aging, in less than 7 days, and likewise lost their color in both room temperature and 49° C. aging.

Set time of the liquid samples aged at room temperature and 49° C. are presented in Table 8. A control sample of PR01 had an initial set time of 5-6 seconds and as room temperature aging proceeded, at all test times between 14 and 56 days, a set time of approximately 3 seconds was observed. The data in Table 8 show that commercial cyanoacrylate containing dye masterbatches based on a variety of acids, cured the same as the control from which they were formulated, thus the presence of the dye masterbatch in PR01 did not alter cure speed. All of these inventive samples bleached from deep blue to colorless as they cured in the set time test.

TABLE 8

Set Time of Color-Change Cyanoacrylate Samples Aged at Room Temperature and 49° C.

| Sample ID | Stabilizing Acid | Initial | Set Time (sec) after RT Aging | | | Set Time (sec) after 120° F. Aging | | |
|---|---|---|---|---|---|---|---|---|
| | | | 14 day | 28 day | 56 day | 14 day | 28 day | 56 day |
| 2A | boron trifluoride etherate | 5-6 | 3 | — | — | 4 | — | — |
| 2B | trifluoromethanesulfonic acid | 5-6 | 3 | 4 | 3 | 2 | 2 | 2 |
| 2C | methylene disulfone | 5-6 | 4 | 4 | 3 | 3 | 1 | 3 |
| 2D | methide acid | 4-5 | 3 | 2 | 2 | 2 | 2 | 3 |
| 2E | imide acid | 5-6 | 3 | 4 | 4 | 3 | 2 | 2 |
| 2F | ethylimide acid | 5-6 | 3 | 3 | 4 | 2 | 2 | 2 |
| 2G | trifluoromethanesulfonic anhydride | 5-6 | 3 | 3 | — | 2 | 3 | 10 |

Example 3

This example examines stability of a series of color change cyanoacrylates containing various ratios of triflic acid and methanesulfonic acid. Two dye masterbatches were prepared employing the components and quantities (in parts by weight) shown in Table 9 to provide samples having acid/dye mol ratio of approximately 2/1 and containing approximately 3000 ppm dye. These dye masterbatches were then blended with each other to provide the mol ratios of triflic acid content shown in Table 10 (in parts by weight).

TABLE 9

Dye Masterbatches

| Example | Acid | PR01 | MSA Concentrate | TFMSA Concentrate | Dye Base Concentrate A |
|---|---|---|---|---|---|
| 3A-Master | methanesulfonic acid (98%) | 9.54 | 0.213 | — | 0.3 |
| 3E-Master | trifluoromethanesulfonic acid | 9.43 | — | 0.333 | 0.3 |

TABLE 10

Dye Master Batches

| Example | 3A-Master | 3E-Master | Triflic Acid Content - Mol % of Total Acid |
|---|---|---|---|
| 3B-Master | 3.75 | 1.25 | 0.25 |
| 3C-Master | 2.50 | 2.50 | 0.50 |
| 3D-Master | 1.25 | 3.75 | 0.75 |

Five color change cyanoacrylate compositions were prepared from these 5 dye masterbatches by blending 0.25 pt of each with 9.75 pt PR01 as described in Example 1 to obtain samples containing approximately 75 ppm dye. The samples thus prepared were all deep blue in color and were checked for set time then aged at room temperature and assessed after 16 days for any change in color or viscosity. These results are presented in Table 11, which show that stability increases, with respect to color and viscosity, as the ratio of triflic acid/methane sulfonic acid in the samples increases, i.e., as methanesulfonic acid, and so the nucleophilic anion content, decreases.

TABLE 11

Room Temperature Aged Color change Cyanoacrylate

| Example | Triflic Acid Content - Mol % of Total Acid | Initial Set Time (sec) | 16 Day Viscosity | 16 Day Color |
|---|---|---|---|---|
| 3A | 0.00 | 3 | gel | 0 |
| 3B | 0.25 | 3 | gel | 0 |
| 3C | 0.50 | 3 | high visc | 1 |
| 3D | 0.75 | 3 | liquid | 3 |
| 3E | 1.00 | 2 | liquid | 3 |

Example 4

This example examines the effect of accelerant on the set time and bleaching speed of a color change cyanoacrylate. In this example 0.13 g dye masterbatch 3E-Master, having acid/dye mol ratio of approximately 2/1 and containing approximately 3000 ppm dye Michler's hydrol cation, was added to a 5 g bottle of SCOTCH Super Glue Liquid and mixed well to obtain a deep blue colored sample containing approximately 75 ppm dye. The set time of this color change cyanoacrylate and an AD110 control were measured as described in the Test Method section with the exception that the test was conducted on LEXAN polycarbonate. The set time on polycarbonate (hereinafter "PC") was found to be quite long and protracted, i.e., rather than the quick rigid set observed on glass; the set time on PC was more a continuum where the coupons could be moved easily initially, then with more difficulty as viscosity increased, and finally to a stiff stage where the coupons could still be moved but required significant force to move. In the time frame of 1-3 minutes after bond closure increasing viscosity of the adhesive could be detected, by 10-15 minutes the bond strength was building significantly, but the coupons could still be moved with moderate hand force. Probing of the bond strength was discontinued at 15 minutes. The dye-containing sample progressed toward cure slightly faster than did the control adhesive throughout all phases of cure. With respect to color change during the 15 minutes of observation, the bonded area of both samples became cloudy, due to the PC imbibing the monomer, and slightly grey in color, with the exception that the dye-containing sample was a light blue-grey color. After standing for 16 hr in a constant temperature and humidity room (CTH), at 22° C. and 50% RH, the samples appeared fully cured and the faint blue hue had vanished from the dye-containing sample.

The next experiment undertaken examined the effect of a cure accelerant on the cure speed of the dye-containing sample. One of the PC coupons was misted with PRONTO Surface Activator, by depressing the spray bottle pump mechanism one time, and allowing the accelerator to dry for a few minutes. Cyanoacrylate was applied to the uncoated coupon and the bond was closed immediately. A set time of 3-4 seconds was recorded with the sample bleaching colorless immediately upon cure. In this case the bonded area was clear and did not exhibit the cloudy appearance observed above when no accelerator was employed. The above findings show that by employing an appropriate accelerant, the set time and bleach speed on PC of colored cure indicating of the present disclosure can be reduced from many minutes to a matter of seconds.

Example 5

This example examines the effect of dye concentration on set time and color stability of cyanoacrylate gel. The components employed to prepare the samples of this composition were dye masterbatch 3E-Master, having acid/dye mol ratio of approximately 2/1 and containing approximately 3000 ppm Michler's hydrol cation, and CA-50 gel, used in the proportions (in parts by weight) shown in Table 12. Sample 5D consisted of 1 pt sample 5A and 8 pt CA-50 gel and provided a dye content of approximately 5 ppm. The samples were formulated by hand mixing, with a spatula, the appropriate ratio of gel and dye masterbatch, and transferring the homogenous blue colored cure-indicating gel to a polypropylene container. Sample color and set time were assessed using the tests described in the Test Methods section and are presented in Table 12. The data show that the color intensity of the gels decreased with decreasing dye concentration. All of the samples bleached colorless during the set time test. A sample of the neat colorless gel was tested for set time and found to have set time of 16 seconds, thus the presence of dye in Examples 5A to 5D did not slow the set time.

TABLE 12

Color Change Cyanoacrylate Gel

| Sample ID | CA-50 Gel | 3E-Master | Dye Conc in Gel (ppm) | Color | Set Time (Sec) |
|---|---|---|---|---|---|
| 5A | 9.85 | 0.1500 | 45 | 2.0 | 13 |
| 5B | 9.90 | 0.1000 | 30 | 1.5 | 13 |
| 5C | 9.95 | 0.0500 | 15 | 1.0 | 12 |
| 5D | — | — | 5 | 0.5 | 12 |

Example 6

This example examines the effect of acid/dye ratio on stability of color change cyanoacrylate compositions. In this series, dye concentrates consisting of PR01, triflic acid, and Michler's hydrol were prepared by the procedure described in Example 1 using the components in the proportions (in parts by weight) shown in Table 13 to obtain dye masterbatches containing approximately 3000 ppm dye.

TABLE 13

Dye Masterbatches

| Sample ID | Acid/Dye mol Ratio | PR01 | TFMSA Concentrate | Dye Concentrate A |
|---|---|---|---|---|
| 6A-Master | 2.5 | 9.36 | 0.416 | 0.3 |
| 6B-Master | 2.0 | 9.43 | 0.333 | 0.3 |
| 6C-Master | 1.5 | 9.51 | 0.250 | 0.3 |
| 6D-Master | 1.0 | 9.58 | 0.167 | 0.3 |

The masterbatches of Table 13 were further formulated with PR01 to provide the color change cyanoacrylates of Table 14 by combining 0.25 pt masterbatch with 9.75 pt PR01, as described in Example 1, to obtain samples containing approximately 75 ppm dye. Color and set time of the samples were assessed as described in the Test Methods section and are reported in Table 14.

TABLE 14

Acid/Dye Ratios

| Sample ID | Masterbatch Acid/Dye mol Ratio | Color | Set Time | Set Time Bleach |
|---|---|---|---|---|
| 6A | 2.5 | 2.75 | 4 | colorless |
| 6B | 2.0 | 2.75 | 5 | colorless |
| 6C | 1.5 | 3 | 5 | colorless |
| 6D | 1.0 | 3 | 7 | colorless |

Example 7

This Example examines the effect of dye concentration on set time, color, and bleaching of color change cyanoacrylate compositions. In this Example a dye masterbatch consisting of PR01, triflic acid, and Michler's hydrol was prepared by the procedure described in Example 1, employing 9.43 pt PR01, 0.333 pt TFMSA Concentrate, and 0.3 pt dye base concentrate A, to obtain dye masterbatches having an acid/dye mol ratio of approximately 2/1 and containing approximately 3000 ppm dye. The dye masterbatches were further formulated with PR01 to provide the color change cyanoacrylates of Table 15 using the proportions (in parts by weight) disclosed therein. Color, set time, and bleaching of the samples were assessed as described in the Test Methods section and are reported in Table 15. Samples 7D through 7F were considerably darker than the reference solutions, thus were labeled 3+. Set time results show that no cure inhibition is observed and that all the samples have essentially the same set time. All of the samples bleached colorless in the Set Time Test.

TABLE 15

| Sample | Dye Content (ppm) | PRO-1 | Dye Masterbatch | Color | Set Time | Set Time Bleach |
|---|---|---|---|---|---|---|
| 7A | 10 | 9.97 | 0.0333 | 2 | 5 | colorless |
| 7B | 50 | 9.83 | 0.1667 | 2.75 | 5 | colorless |
| 7C | 100 | 9.67 | 0.3333 | 3 | 5 | colorless |
| 7D | 250 | 9.17 | 0.8333 | 3+ | 5 | colorless |
| 7E | 500 | 8.33 | 1.6667 | 3+ | 5-6 | colorless |
| 7F | 1000 | 6.67 | 3.3333 | 3+ | 4-6 | colorless |

Examples 8 and 9

In these Examples two color change cyanoacrylate compositions were prepared that changed from a first colored state to a second colored state, and did not exhibit the colored to colorless transition state, exhibited as the cyanoacrylate-based adhesive progresses from an uncured state to a cured state, of many of the previous examples. Example 8 contained the bleachable dye of Michler's hydrol and the non-indicator dye 1,8-dihydroxyanthraquinone. Example 9 contained two color-change dyes, that of Michler's hydrol, and methyl yellow (4-(dimethylamino)azobenzene).

Example 8 employed two different dye solutions. The bleachable dye solution was 3E-Master, containing triflic acid and Michler's hydrol in PR01 having an acid/dye mol ratio of 2/1 and a dye content of 3000 ppm. The non-bleachable dye solution contained 38.92 pt SB20 and 1.2 pt of a 10% solution of 1,8-dihydroxyanthraquinone in methyl acetate, to provide a non-indicating dye content of approximately 3000 ppm. To 9.67 pt of the non-bleachable dye solution was added 0.333 pt of 3E-Master, to provide a bright green color change cyanoacrylate composition having a 1,8-dihydroxyanthraquinone dye content of approximately 2900 ppm and a Michler's hydrol cation content of approximately 100 ppm. This sample was tested for set time as described in the Test Methods section and provided a set time of 1-2 seconds, which was the same as the parent SB20 adhesive. As this cyanoacrylate-based adhesive progressed from an uncured state to a cured state, the color changed almost instantaneously from green to bright yellow.

Example 9 employed two different dye solutions, both of which contained indicating dyes. The first dye solution consisted of the Michler's hydrol cation masterbatch of Example 1 based on PR01, triflic acid, and Michler's hydrol, and had an acid/dye mol ratio of approximately 2.2/1 and a dye content of approximately 3000 ppm.

The second dye solution was prepared as in Example 1 by combining 9.25 pt PR01, 0.2 pt TFMSA Concentrate, and 0.6 pt of a 5% solution of methyl yellow in methyl acetate to provide a methyl yellow dye concentrate having an acid to dye mol ratio of 1/1 and a dye content of 3000 ppm.

The adhesive composition was prepared by combining 8.08 pt PR01, 0.25 pt Michler's hydrol cation masterbatch, and 1.67 pt methyl yellow dye concentrate, to provide a color change cyanoacrylate composition containing approximately 75 ppm Michler's hydrol and 500 ppm methyl yellow. This sample was tested for set time as described in the Test Methods section and provided a set time of approximately 5 seconds, which was the same as the parent PR01 adhesive. As this cyanoacrylate-based adhesive progressed from an uncured state to a cured state, the color changed from an initial deep red color to an intermediate green and finally to a light orange color.

Example 10

This example demonstrates that a medical grade butyl cyanoacrylate adhesive can be converted to a color change adhesive composition by addition of a Michler's hydrol dye masterbatch. The dye masterbatch and color change cyanoacrylate adhesive were prepared as described in Example 1 by first formulating a 10 wt % dye base solution of Michler's hydrol in methyl acetate and a 10 wt % acid solution of triflic acid in NEXCARE props Liquid Bandage (NDLB). The 10 wt % dye solution contained 1.35 pt methyl acetate and 0.15 pt Michler's hydrol. The acid solution contained 1.8 pt NDLB and 0.2 pt triflic acid. The dye masterbatch contained 9.46 pt NDLB, 0.30 pt 10% triflic acid solution, and 0.30 pt 10% dye solution which resulted in a dye masterbatch having an acid/dye mol ratio of approximately 1.8/1 and a dye content of approximately 3000 ppm dye.

The adhesive composition was prepared by combining 9.75 pt NDLB and 0.25 pt dye masterbatch to provide a color change medical grade cyanoacrylate adhesive composition containing approximately 75 ppm dye. This deep blue sample was tested for set time as described in the Test Methods section and provided a set time of approximately 3-4 seconds, which was the same as the parent NDLB adhesive. As this cyanoacrylate-based adhesive progressed from an uncured state to a cured state in the set time test, the color changed from an initial deep blue color to colorless. A drop of this adhesive composition was applied to the skin of a human hand, spread with a cotton-tipped applicator to provide a thin uniform layer, and observed for color change and set time. In approximately 1 minute the adhesive bleached colorless and was dry to the touch.

Example 11

This example displays the Strength Ratio of a variety of acids with various nitrated aniline Acidity Indicators using the procedures described in the Test Methods section of this disclosure. The results are given in Table 16 and show the differentiation between workable and nonworkable acids in the instant invention.

TABLE 16

Strength Ratio of Various Acids (from Titration)

| Acid | Indicator X | Strength Ratio E | Workable (Y/N) |
| --- | --- | --- | --- |
| $(CF_3SO_2)_2NH$ | 2,6-dinitroaniline | 0.93 | Y |
| $(C_2F_5SO_2)_2NH$ | 2,6-dinitroaniline | 0.93 | Y |
| $CF_3SO_3H$ | 2,6-dinitroaniline | 0.82 | Y |
| $BF_3$:2 acetic acid | 2-chloro-6-nitroaniline | 0.82 | Y |
| $(CF_3SO_2)_3C^-$ $(H_2O)_{16}H^+$ | 4-methoxy-2-nitroaniline | 0.52 | Y |
| $(CF_3SO_2)_2C(H)C_6H_5$ | 4-methoxy-2-nitroaniline | 0.49 | Y |
| $(CF_3SO_2)_2CH_2$ | 4-methoxy-2-nitroaniline | 0.34 | Y |
| $BF_3$:etherate (not buffered) | 2-chloro-6-nitroaniline | 0.30 | Y |
| $BF_3$:2 $CH_3OH$ | 4-chloro-2-nitroaniline | 0.24 | Y |
| Methanesulfonic acid | 4-chloro-2-nitroaniline | <0.01 | N |
| Methanesulfonic acid | 2,6-dinitroaniline | <0.001 | N |
| Methanesulfonic acid | 2-chloro-6-nitroaniline | <0.001 | N |
| $BF_3$:2 $H_2O$ | 4-chloro-2-nitroaniline | 0.14 | N |
| $CF_3CO_2H$ | 4-methoxy-2-nitroaniline | <0.01 | N |

Example 12

This example examines color change properties of various Michler's hydrol dye derivatives. Masterbatches of each dye are made by combining 0.44 pt 10% solution of TFMSA in PR01 with 0.40 pt 10% solution of dye base in THF and mixing well, followed by the addition of 9.16 pt PR01. The resulting dye masterbatches are agitated slowly for 30 minutes to assure homogeneity. Combining 4.91 pt PR01 with 0.094 pt dye masterbatch and agitating slowly for 30 minutes completes the preparation of color change cyanoacrylate samples. The resulting samples are tested by placing 1 drop of color change cyanoacrylate on a first glass microscope slide, placing a second glass slide atop the first and observing after 1 minute to detect cure and note any color change that occurred. Inspecting the samples for cure reveals that all samples cure. Table 17 provides the color change behavior.

TABLE 17

Bleach Behavior of Color Change Cyanoacrylate Compositions

| Sample | Dye Name | Initial Color | Color After Cure |
| --- | --- | --- | --- |
| 12-1 | N-[bis[4-(dimethylamino)phenyl]methyl]-aniline | blue | colorless |
| 12-2 | N-[bis[4-(dimethylamino)phenyl]methyl]-N'-(4-ethoxyphenyl)-urea | blue | colorless |
| 12-3 | N-[bis[4-(dimethylamino)phenyl]methyl]-N'-n-butyl-urea | blue | colorless |
| 12-4 | N-[bis[4-(dimethylamino)phenyl]methyl]-N'-phenyl-urea | blue | colorless |
| 12-5 | N-[bis[4-(dimethylamino)phenyl]methyl]-morpholine | blue | colorless |
| 12-6 | N-[bis[4-(dimethylamino)phenyl]methyl]-benzenesulfonamide | light blue | colorless |
| 12-7 | Bis[4-(4-morpholinyl)phenyl]methanol | blue | colorless |
| 12-8 | 1,1-bis(4-dimethylaminophenyl)ethanol | blue | colorless |
| 12-9 | 1,1-bis(4-dimethylaminophenyl)ethylene | blue | colorless |
| 12-10 | bis(4-(dimethylamino-2-methylphenyl)methanol | blue | colorless |
| 12-11 | bis(3-bromo-4-dimethylaminophenyl)methanol | blue | colorless |

Example 13

This Example examines the effect of acid/dye mol ratio on the behavior of color change cyanoacrylate adhesives. The acids examined were $BF_3:2\ CH_3OH$, $BF_3(AcOH)_2$, and imide acid at acid/dye mol ratios ranging from 1:1 to 5:1. For the two $BF_3$-complexes, the acid/dye mol ratio was based on mols $BF_3$, not mols of the $BF_3$-complexes. Acid/dye masterbatches were formulated by preparing 10 wt % solutions of each acid in SB14 and combining these acid concentrates with Dye Base Concentrate A and SB14 in the ratios shown in Table 18. Specifically, Dye Base Concentrate A was added to acid concentrate and mixed well before SB14 was added and mixed to complete preparation of the acid/dye concentrates. Mixing 0.25 parts of acid/dye concentrate with 9.75 pt SB14 in HDPE bottles completed preparation of the color change cyanoacrylate adhesives.

TABLE 18

Acid/Dye Concentrates

| Sample | Acid | Acid/Dye mol Ratio | SB14 | Dye Base Conc A | Acid Conc |
|---|---|---|---|---|---|
| 13-1-AD | $BF_3(AcOH)_2$ | 1.00 | 9.210 | 0.3 | 0.578 |
| 13-2-AD | $BF_3(AcOH)_2$ | 2.00 | 8.690 | 0.3 | 1.155 |
| 13-3-AD | $BF_3(AcOH)_2$ | 3.00 | 8.170 | 0.3 | 1.733 |
| 13-4-AD | $BF_3(AcOH)_2$ | 4.00 | 7.650 | 0.3 | 2.311 |
| 13-5-AD | $BF_3(AcOH)_2$ | 5.00 | 7.130 | 0.3 | 2.889 |
| 13-6-AD | $BF_3 \cdot 2\ CH_3OH$ | 1.00 | 9.595 | 0.3 | 0.150 |
| 13-7-AD | $BF_3 \cdot 2\ CH_3OH$ | 2.00 | 9.459 | 0.3 | 0.301 |
| 13-8-AD | $BF_3 \cdot 2\ CH_3OH$ | 3.00 | 9.324 | 0.3 | 0.451 |
| 13-9-AD | $BF_3 \cdot 2\ CH_3OH$ | 4.00 | 9.188 | 0.3 | 0.602 |
| 13-10-AD | $BF_3 \cdot 2\ CH_3OH$ | 5.00 | 9.053 | 0.3 | 0.752 |
| 13-11-AD | Imide Acid | 1.00 | 9.449 | 0.3 | 0.312 |
| 13-12-AD | Imide Acid | 2.00 | 9.168 | 0.3 | 0.624 |
| 13-13-AD | Imide Acid | 3.00 | 8.888 | 0.3 | 0.936 |
| 13-14-AD | Imide Acid | 4.00 | 8.607 | 0.3 | 1.248 |
| 13-15-AD | Imide Acid | 5.00 | 8.326 | 0.3 | 1.560 |

Sample 13-6, based on $BF_3:2\ CH_3OH$ and having acid/dye mol ratio of 1:1, gelled shortly after preparation, and Sample 13-11, based on imide acid and having an acid/dye mol ratio of 1:1 gelled sometime between 1 and 2 weeks while aging at room temperature. The color stability of the adhesives was assessed after aging them for various lengths of time at room temperature as shown in Table 19. For each acid, increased acid/dye ratios resulted in increased bleach times.

TABLE 19

Color of Color Change CA Adhesives Aged at Room Temperature

| Sample | Acid | Acid/Dye mol Ratio | 1 Week Color | 2 Week Color | 3 Week Color |
|---|---|---|---|---|---|
| 13-1 | $BF_3(AcOH)_2$ | 1.00 | 2.75 | 2.75 | 2.75 |
| 13-2 | $BF_3(AcOH)_2$ | 2.00 | 2.75 | 2.5 | 2.5 |
| 13-3 | $BF_3(AcOH)_2$ | 3.00 | 2.75 | 2.5 | 2.5 |
| 13-4 | $BF_3(AcOH)_2$ | 4.00 | 2.5 | 2.25 | 2.25 |
| 13-5 | $BF_3(AcOH)_2$ | 5.00 | 2.5 | 2.25 | 2.25 |
| 13-6 | $BF_3:2\ CH_3OH$ | 1.00 | — | — | — |
| 13-7 | $BF_3:2\ CH_3OH$ | 2.00 | 2.75 | 2.5 | 2.25 |
| 13-8 | $BF_3:2\ CH_3OH$ | 3.00 | 2.75 | 2.5 | 2.25 |
| 13-9 | $BF_3:2\ CH_3OH$ | 4.00 | 2.75 | 2.5 | 2.25 |
| 13-10 | $BF_3:2\ CH_3OH$ | 5.00 | 2.75 | 2.75 | 2.5 |
| 13-11 | Imide Acid | 1.00 | — | — | — |
| 13-12 | Imide Acid | 2.00 | 2.75 | 3 | 2.75 |
| 13-13 | Imide Acid | 3.00 | 2.25 | 2.5 | 2.25 |
| 13-14 | Imide Acid | 4.00 | 2 | 2 | 2 |
| 13-15 | Imide Acid | 5.00 | 1.5 | 1.5 | 1.5 |

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

We claim:

1. A cyanoacrylate-based adhesive composition comprising:
   a cyanoacrylate monomer; and
   a bleachable dye comprising Michler's hydrol cation, or derivatized Michler's hydrol cation, paired with a non-nucleophilic anion that provides a stable color to the cyanoacrylate-based adhesive.

2. A cyanoacrylate-based adhesive composition according to claim 1 wherein the bleachable dye is Michler's hydrol cation.

3. A cyanoacrylate-based adhesive composition according to claim 1 wherein the non-nucleophilic anion is derived from a carbon-acid having a strength ratio value greater than 0.1 when measured in sulfolane solvent and using 4-methoxy-2-nitroaniline indicator.

4. A cyanoacrylate-based adhesive composition according to claim 1 wherein the non-nucleophilic anion is derived from a non-carbon-acid having a strength ratio value greater than 0.2 when measured in sulfolane solvent and using 4-chloro-2-nitroaniline indicator.

5. A cyanoacrylate-based adhesive composition according to claim 1 wherein the non-nucleophilic anion is derived from boron trifluoride methanol, trifluoromethanesulfonic acid, methide acid, imide acid, ethylimide acid, boron trifluoride acetic acid, or mixtures thereof.

6. A cyanoacrylate-based adhesive composition according to claim 1 wherein the Michler's hydrol cation or derivatized Michler's hydrol cation is present in the cyanoacrylate-based adhesive in at least 1 ppm and the non-nucleophilic anion is present in the cyanoacrylate-based adhesive at a non-nucleophilic anion/dye mol ratio of 1 to 5.

7. A cyanoacrylate-based adhesive composition according to claim 1 further comprising a colorant.

8. A cyanoacrylate-based adhesive composition according to claim 1 further comprising a thickener.

* * * * *

UNITED STATES PATENT AND TRADEMARK OFFICE
CERTIFICATE OF CORRECTION

PATENT NO. : 8,217,110 B2
APPLICATION NO. : 11/850873
DATED : July 10, 2012
INVENTOR(S) : Kurt Charles Melancon et al.

It is certified that error appears in the above-identified patent and that said Letters Patent is hereby corrected as shown below:

Cover Page Column 2 (Other Publications)
Line 5, delete "html<" and insert -- html> --, therefor.

Line 28, delete "Sulfanel[1]" and insert -- "Sulfolane[1]" --, therefor.

Column 7
Line 26, delete "Extinction Ratio=∈*/∈==N" and insert -- Extinction Ratio = ε*/ε = N --, therefor.

Column 8
Line 48, delete "tetrahydrofulfuryl" and insert -- tetrahydrofurfuryl --, therefor.

Column 15
Line 3, delete "morality" and insert -- molality --, therefor.

Column 16
Line 35 (approx.), delete "value" and insert -- ε value --, therefor.

Column 17
Line 39 (approx.), delete "Scotchweld" and insert -- SCOTCH-WELD --, therefor.

Line 56, delete "'props" and insert -- Drops --, therefor,

Line 58, delete "55144" and insert -- 55144. --, therefor.

Column 18

Line 37, delete "Lexan™" and insert -- LEXAN --, therefor.

Line 40 (approx.), delete "Pronto™" and insert -- PRONTO --, therefor.

Signed and Sealed this
Twenty-ninth Day of January, 2013

David J. Kappos
*Director of the United States Patent and Trademark Office*

Column 19
Line 59, delete "SCOTCHWELD" and insert -- SCOTCH-WELD --, therefor.

Column 21
Line 11, delete "C21" and insert -- C2I --, therefor.

Column 29
Line 28, delete "props" and insert -- Drops --, therefor.